United States Patent
Ahn

(10) Patent No.: US 8,034,768 B2
(45) Date of Patent: Oct. 11, 2011

(54) COMPOSITION AND METHOD FOR THE TREATMENT OF DISEASES AFFECTED BY HISTONE DEACETYLASE INHIBITORS

(75) Inventor: Jung-Mo Ahn, Richardson, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 338 days.

(21) Appl. No.: 12/144,425

(22) Filed: Jun. 23, 2008

(65) Prior Publication Data

US 2008/0318844 A1    Dec. 25, 2008

Related U.S. Application Data

(60) Provisional application No. 60/945,910, filed on Jun. 23, 2007.

(51) Int. Cl.
*A61K 38/12* (2006.01)
*A61K 38/55* (2006.01)

(52) U.S. Cl. .......................................... 514/2.9; 514/4.1

(58) Field of Classification Search .................. None
See application file for complete search history.

(56) References Cited

U.S. PATENT DOCUMENTS

| | | | |
|---|---|---|---|
| 7,041,639 B2 | 5/2006 | Skov | |
| 7,091,229 B2 | 8/2006 | Georges et al. | |
| 7,098,186 B2 | 8/2006 | Nagai et al. | |
| 7,314,862 B2 | 1/2008 | Naoe et al. | |
| 2005/0176686 A1 | 8/2005 | Maurer et al. | |
| 2005/0209134 A1 | 9/2005 | Nagai et al. | |
| 2006/0128660 A1 | 6/2006 | Rajski et al. | |
| 2006/0135413 A1 | 6/2006 | Naoe et al. | |
| 2006/0269559 A1 | 11/2006 | Jackson et al. | |
| 2007/0117848 A1 | 5/2007 | Puerta et al. | |
| 2007/0129290 A1 | 6/2007 | Or et al. | |

FOREIGN PATENT DOCUMENTS

WO    2007/040522 A1    4/2007

OTHER PUBLICATIONS

Ahn, J.-M., et al., "Peptidomimetics and peptide backbone modifications." Mini-Reviews in Medicinal Chemistry (2002), 2:463-473.
Ahn, S. H., et al., "Sterile 20 kinase phosphorylates histone H2B at serine10 during hydrogen peroxide induced apoptosis in S. cerevisiae." Cell (2005), 120:25-36.
Cao, H., et al., "Induction of human gamma globin gene expression by histone deacetylase inhibitors." Blood (2004), 103:701-709.
Di Maro, S., et al., "Development of an Efficient Solid-Phase Synthetic Methodology to Construct a Combinatorial Library of a Potent HDAC Inhibitor," (Abstract) 2007 APS Symposium.
Furumai, R., et al., "FK228 (Depsipeptide) as a Natural Prodrug That Inhibits Class I Histone Deacetylases," Cancer Research (2002), 62:4916-4921.
Holbert, M., et al., "Structure and activity of enzymes that remove histone modifications," Curr Op Struc Biol (2005), 15:673-680.
Liu, T., et al., "Histone deacetylase inhibitors: Multifunctional anti-cancer agents," Cancer Treatment Reviews (2006), 32:157-165.
Monneret, C., "Histone deacetylase inhibitors," Eur J Med Chem (2005), 40:1-13.
Peedicayil, J. "Epigenetic therapy—a new development in pharmacology." Indian J. Med. Res. (2006), 123:17-24.
Somoza, J. R., et al., "Structural snapshots of human HDAC8 provide insights into the class I histone deacetylases." Structure (2004), 12:1325-1334.
Vannini, A., et al., "Crystal structure of a eukaryotic Zn-dependent histone deacetylase, human HDAC8, complexed with a hydroxamide acid inhibitor." Proc. Natl. Acad. Sci. U.S.A. (2004), 101:15064-15069.
Wang, D-F., et al., "Toward Selective Histone Deacetylase Inhibitor Design: Homology Modeling, Docking Studies, and Molecular Dynamics Simulations of Human Class I Histone Deacetylases," J Med Chem (2005), 48:6936-6947.
Yamada, H., et al., "Depsipeptide-resistant KU812 cells show reversible P-glycoprotein expression:hyper-acetylated histones, and modulated gene expression profile." Leukemia Res. (2006), 30:723-734.
International Search Report and Written Opinion for PCT/US2008/067924 dated Sep. 11, 2008.

*Primary Examiner* — Cecilia J Tsang
*Assistant Examiner* — Satyanarayana Gudibande
(74) *Attorney, Agent, or Firm* — Chainey P. Singleton; Edwin S. Flores; Chalker Flores, LLP

(57) ABSTRACT

The present invention includes methods of treatment and compositions for treating diseases related to the activity of a histone deacetylase in a subject by administering to the subject an effective amount of a modified FK228 compound comprising an amino acid conjugate which constitutes an amino thiol, a hydroxy thiol, a dithiol, or a hydroxamic acid, instead of a hydroxy-mercapto-heptenoic acid moiety in FK228.

4 Claims, 19 Drawing Sheets

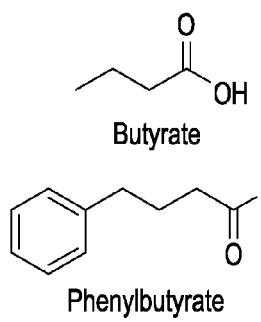
FIG. 1A
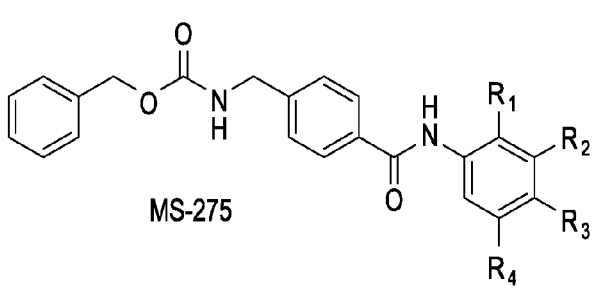
FIG. 1B
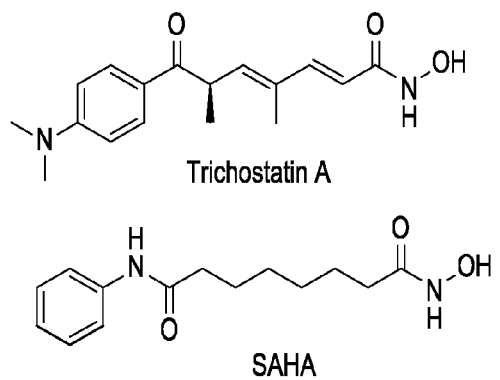
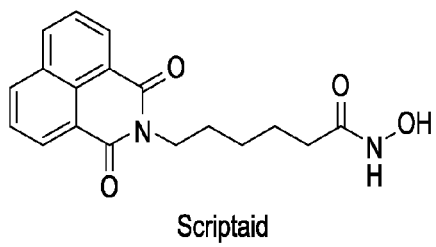
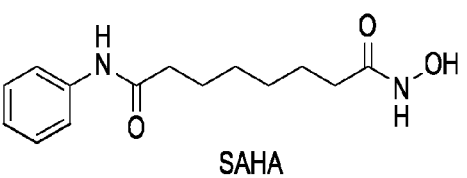
FIG. 1C
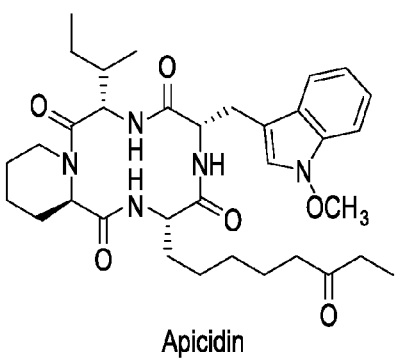
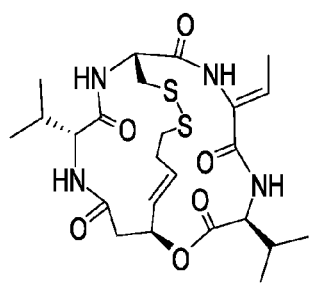
FIG. 1D
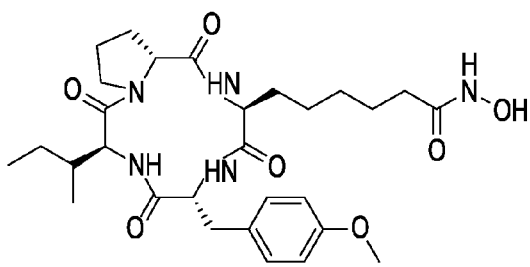

A    B

C    D

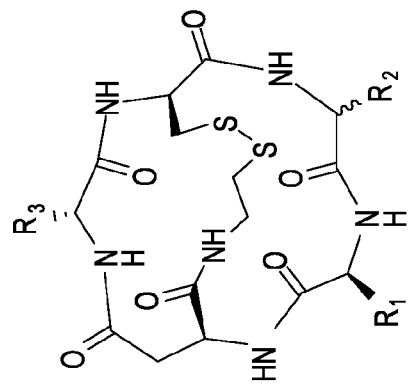
FIG. 10A
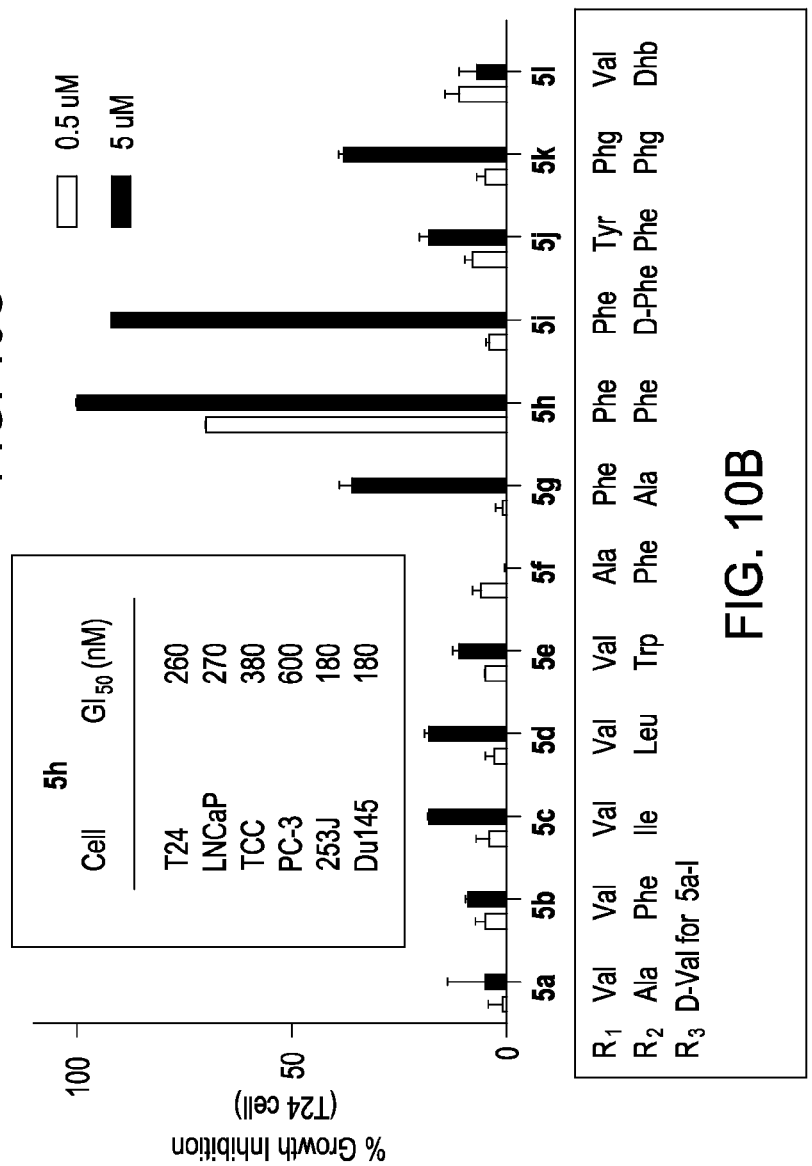
FIG. 10C
FIG. 10B

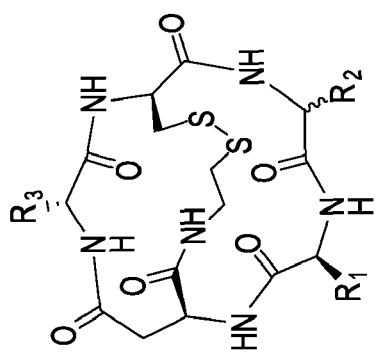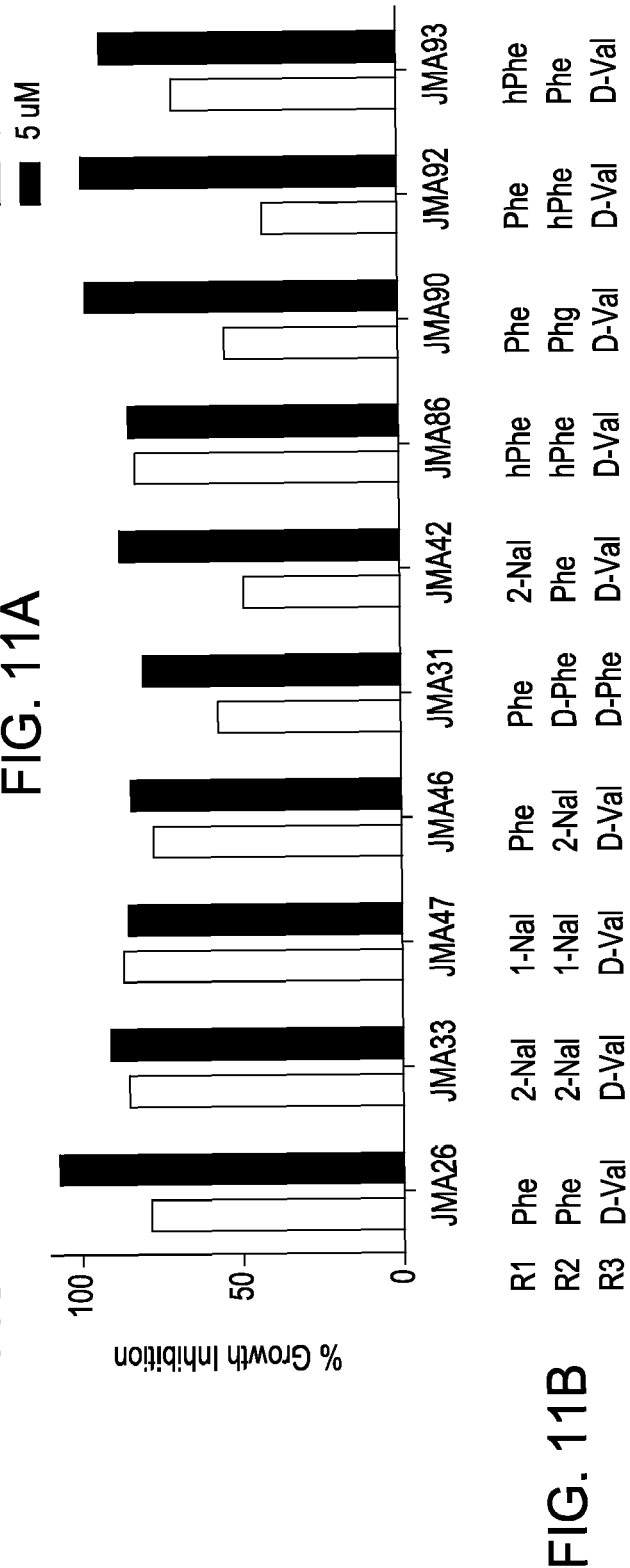
FIG. 11A
FIG. 11B
FIG. 11C

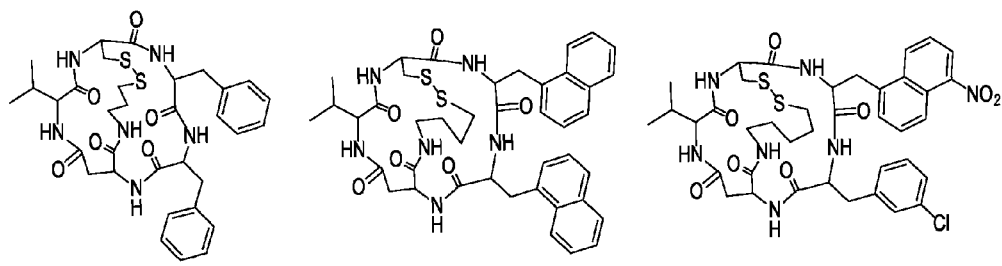
FIG. 12QQ  FIG. 12RR  FIG. 12SS
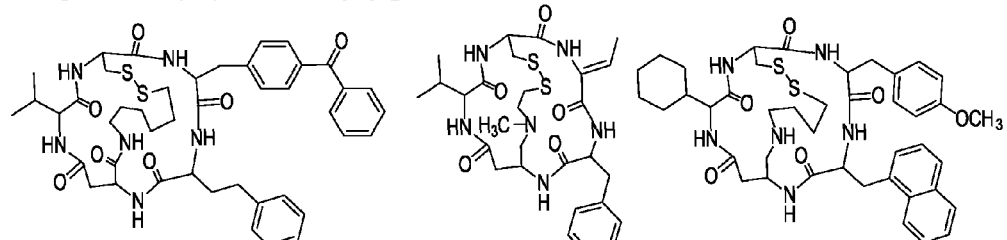
FIG. 12TT  FIG. 12UU  FIG. 12VV
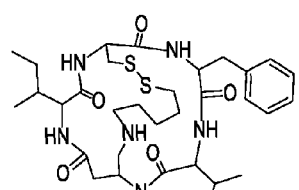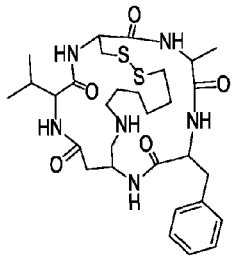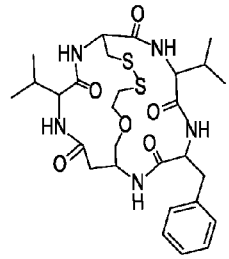
FIG. 12WW  FIG. 12XX  FIG. 12YY
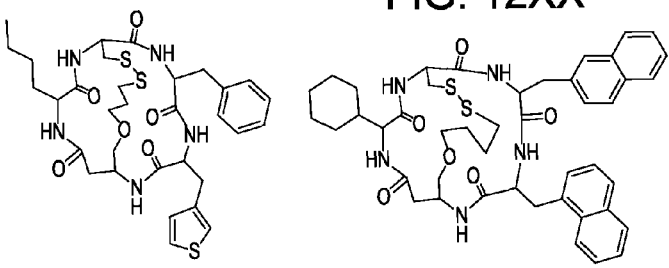
FIG. 12ZZ  FIG. 12AAA  FIG. 12BBB
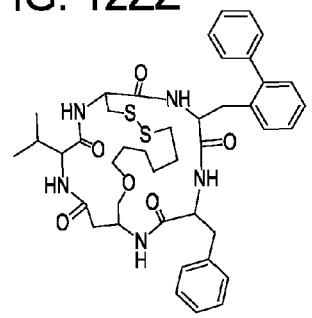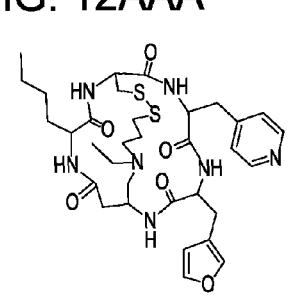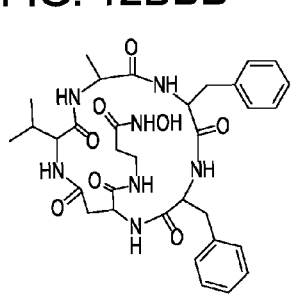
FIG. 12CCC  FIG. 12DDD  FIG. 12EEE

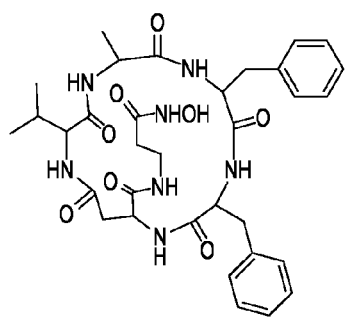
FIG. 12FFF
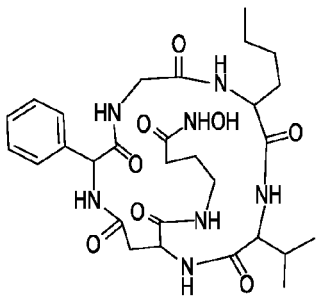
FIG. 12GGG
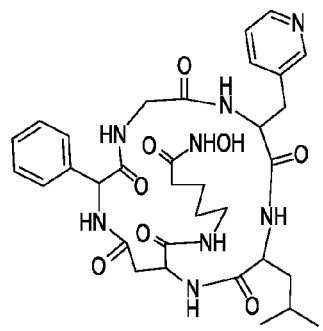
FIG. 12HHH
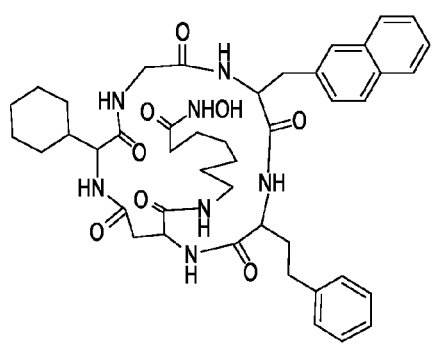
FIG. 12III
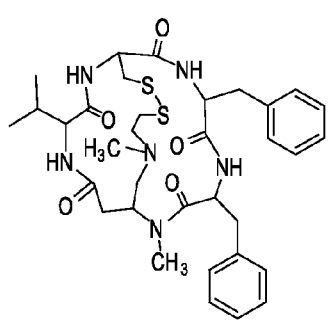
FIG. 12JJJ
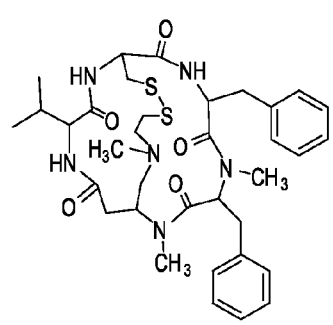
FIG. 12KKK
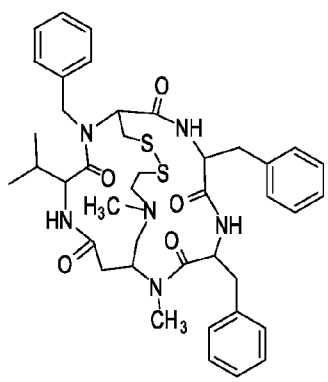
FIG. 12LLL
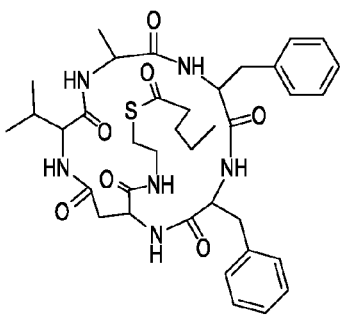
FIG. 12MMM
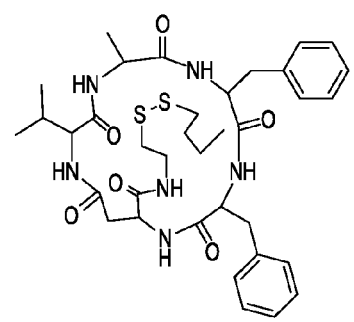
FIG. 12NNN

US 8,034,768 B2

COMPOSITION AND METHOD FOR THE TREATMENT OF DISEASES AFFECTED BY HISTONE DEACETYLASE INHIBITORS

CROSS-REFERENCE TO RELATED APPLICATIONS

This application claims priority to U.S. Provisional Application Ser. No. 60/945,910, filed Jun. 23, 2007, the contents of which are incorporated by reference herein in its entirety.

TECHNICAL FIELD OF THE INVENTION

The present invention relates in general to the field of histone deacetylase inhibitors and specifically to compositions of matter and methods of making and using FK228 analogues for the treatment of diseases.

BACKGROUND OF THE INVENTION

Without limiting the scope of the invention, its background is described in connection with histone deacetylase inhibitors, in particular, structural analogs of compounds related to a histone deacetylase inhibitor known as FK228 or depsipeptide. In the cell, DNA is packaged in the form of chromatin and serves as a dynamic scaffold to regulate various nuclear processes including DNA transcription, replication, repair, mitosis and apoptosis. Chromatin includes 147 base pairs of DNA is wrapped around an octamer of four core histone proteins. Histones are integral and dynamic components of the gene transcriptional machinery and offer a potential regulation points for gene therapy. Specifically, acetylation of specific residues has been associated with active chromatin regions and has been linked to active gene transcription. As such, the histone deacetylase family of enzymes playing an important role in gene expression and have been implicated in cell-cycle arrest and induced differentiation.

For example, the U.S. patent application publication number 20050209134 entitled "novel depsipeptide compound" described a compound which is useful as an agent for prevention and treatment of diseases associated with HDAC, in particular, tumor or cell proliferative diseases. The depsipeptide compound or its pharmaceutically acceptable salt in the '134 application has a good HDAC inhibitory activity and an inhibitory activity of cell proliferation against human cancer cells and, therefore, is useful in treatment and improvement of diseases and pathogenic conditions associated with histone acetylation, in particular, tumor or cell proliferative diseases.

Yet another example can be found in the U.S. patent application publication number 20070129290 that relates to HDAC inhibitor derivatives. The derivatives of the free thiol of metabolites of the HDAC inhibitor FK228, pharmaceutical compositions thereof, and to methods of using such derivatives and pharmaceutical compositions thereof in the treatment of diseases associated with HDAC, in particular, tumor or cell proliferation diseases.

U.S. Pat. No. 7,098,186 teaches a depsipeptide compound which is useful as an agent for prevention and treatment of diseases associated with HDAC, in particular, tumor or cell proliferative diseases. The depsipeptide compound or its pharmaceutically acceptable salt has a good HDAC inhibitory activity and an inhibitory activity of cell proliferation against human cancer cells and, therefore, is useful in treatment and improvement of diseases and pathogenic conditions associated with histone acetylation, in particular, tumor or cell proliferative diseases.

A histone deacetylase inhibitor called as depsipeptide (also known as FK228) is originally isolated from *Chromobacterium violaceum*, and is an exceptionally potent antitumor agent. However, despite its promising in vivo activity, only limited structure-activity relationship study have been carried out presumably resulting from its synthetic difficulties. Its reported synthesis involved 19 steps with an overall yield of about 18% by highly skilled artisans. Its synthetic difficulties prevented traditional structure-activity study of depsipeptide to discover more potent and selective analogues toward various cancer cell lines. In addition, depsipeptide has been found to be extremely cytotoxic and nonspecific in action with little specificity between normal and tumor cells. These challenges have not been met with any solutions and prevented further attempts of improving its potency, selectivity, and pharmacokinetic profile since its derivatives have not been prepared at all.

Thus, the present inventor recognized that there is a need to design novel structural analogues of FK228 so that a large number of compounds can be produced with high efficiency, and with significantly less side effects while high potency is retained.

SUMMARY OF THE INVENTION

The present inventor recognized that the histone deacetylase family of enzymes play an important role in gene expression and therefore a pharmaceutical composition that targets histone deacetylase would initiate cell-cycle arrest and induced differentiation. The present inventor recognized that histone deacetylase inhibitors can be used as a treatment for various cancers and sickle cell disease, e.g., histone deacetylase inhibitors effect tumor cell proliferation, programmed cell death, differentiation and angiogenesis. However, most of histone deacetylase inhibitors (including FK228) are strongly cytotoxic and non-selective, which results in numerous side effects for the therapeutic treatment. The present inventor recognized what was needed was a histone deacetylase inhibitor that was less cytotoxic and had a high selectivity between normal and tumor cells and also towards different cancer cell lines.

The present inventor recognized that this sort of target discrimination is achieved by varying the structure of the most potent histone deacetylase inhibitor, FK228. However, until the present invention the traditional approach of drug discovery could not be applied to this histone deacetylase inhibitor due to high synthetic challenges found in the construction of the histone deacetylase inhibitor and analogues as a result of unnatural building blocks employed in the structure of FK228. These difficulties also prevented further improvement of its potency, selectivity, and pharmacokinetic profile since its analogues could not be prepared easily. The present invention provides structural modifications, analogues and derivatives of FK228. The present invention provides surrogates or modified compounds that enable rapid production as well as facile changes in structure. In addition, the structural modification of the present invention does not alter the global structure of FK228 in order to retain high potency. Furthermore, the present invention provides modifications and analogues with various functional groups positioned at several different sites of FK228. The present invention provides a method of treating diseases related to the activity of a histone deacetylase in a subject by administering to the subject an effective amount of a modified FK228 compound includes an amino acid and an amino thiol conjugate instead of a hydroxy-mercapto-heptenoic acid moiety in FK228.

The present invention also provides a method for modifying histone deacetylase activity in a subject by administering to the subject a modified FK228 compound having an amino acid and an amino thiol conjugate instead of a hydroxy-mercapto-heptenoic acid moiety in FK228, wherein administering the histone deacetylase inhibitor compound modifies the histone deacetylase activity in one or more cells.

A modified FK228 compound having an amino acid conjugate which constitutes an amino thiol, a hydroxy thiol, a dithiol, or a hydroxamic acid, instead of a hydroxy-mercapto-heptenoic acid moiety in FK228 is also provided by the present invention.

The present invention also provides a method for treating a subject that would medically benefit from either stimulation or inhibition of one or more histone deacetylases by administering to the subject a pharmaceutically effective amount of a modified FK228 compound having an amino acid conjugate which constitutes an amino thiol, a hydroxy thiol, a dithiol, or a hydroxamic acid, instead of a hydroxy-mercapto-heptenoic acid moiety in FK228. The modified FK228 compound functions to stimulate or inhibit the activity of one or more histone deacetylases.

The present invention provides a modified FK228 pharmaceutical compound having a therapeutically effective amount of a modified FK228 compound, a salt, a solvate, or a derivative thereof comprising an amino acid conjugate which constitutes an amino thiol, a hydroxy thiol, a dithiol, or a hydroxamic acid, instead of a hydroxy-mercapto-heptenoic acid moiety in FK228 and one or more pharmaceutically acceptable carriers.

The present invention provides a method of treating cancers in a subject by administering to the subject an effective amount of a modified FK228 compound includes an amino acid conjugate which constitutes an amino thiol, a hydroxy thiol, a dithiol, or a hydroxamic acid, instead of a hydroxy-mercapto-heptenoic acid moiety in FK228.

The present invention provides a method of treating sickle cell diseases in a subject by administering to the subject an effective amount of a modified FK228 compound includes an amino acid conjugate which constitutes an amino thiol, a hydroxy thiol, a dithiol, or a hydroxamic acid, instead of a hydroxy-mercapto-heptenoic acid moiety in FK228.

The present invention also provides a compound having the formula:

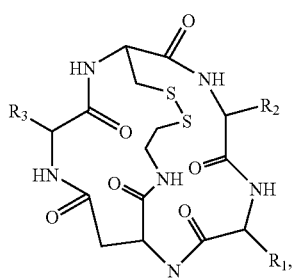

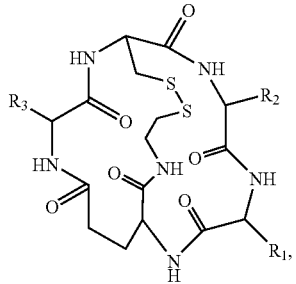

-continued

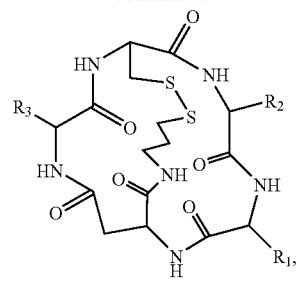

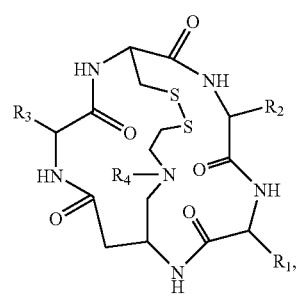

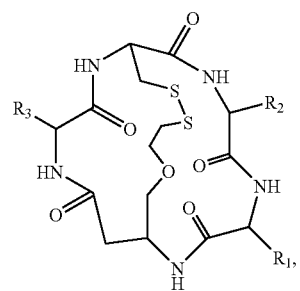

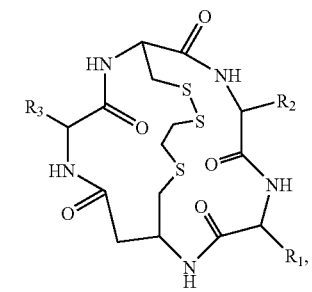

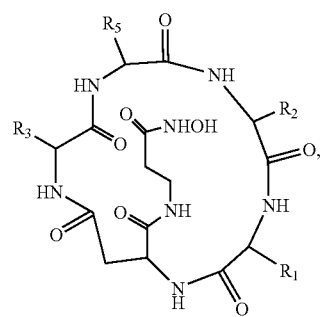

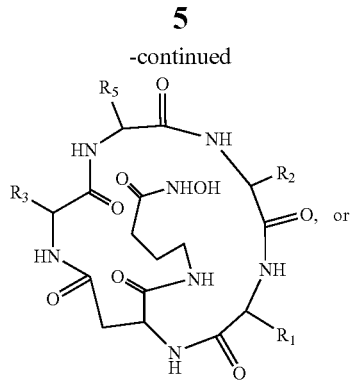

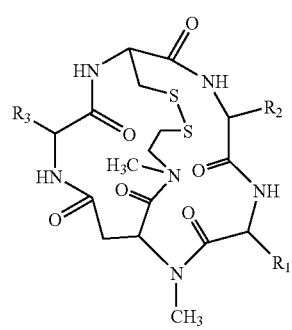

wherein R1-R5 includes independently one or more optionally substituted groups selected from a H, a B, a C, a N, a O, a S, a P, a Se, an lower alkyl, an alkoxy, an alkoxyalkyl, a hydroxy, a hydroxyalkyl, an alkenyl, an amino, an imino, a nitrate, an alkylamino, a dialkylamino, a nitro, a nitroso, an aryl, a biaryl, a polycyclic aromatic, an alkylaryl, an arylalkyl, an arylalkoxy, an arylalkylamino, a cycloalkyl, a bridged cycloalkyl, a cycloalkoxy, a cycloalkyl-alkyl, an arylthio, an alkylthio, an alkylsulfinyl, an alkylsulfonyl, an arylsulfonyl, an arylsulfinyl, a caboxamido, a carbamoyl, a hydroxamate, a carboxyl, a carbonyl, an alkoxycarbonyl, a halogen, a haloalkyl, a haloalkoxy, a heteroayl, a heterocyclic ring, an arylheterocyclic ring, a heterocyclic compound, an amido, an imido, a guanidino, a hydrazido, an aminoxy, an alkoxyamino, an urea, an alkylamido, a carboxylic ester, a thioether, a carboxylic acid, a phosphoryl group, a polycyclic aromatic and combinations thereof.

Similarly the present invention includes a compound having the formulas:

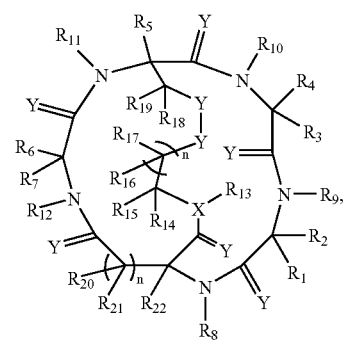

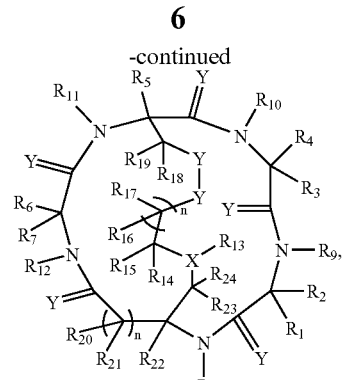

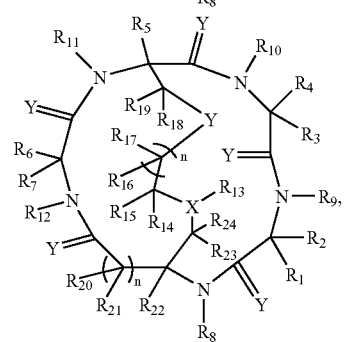

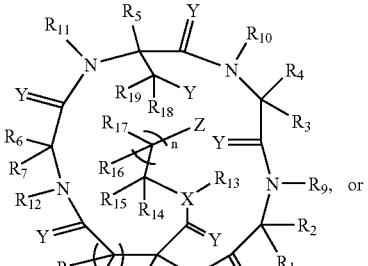

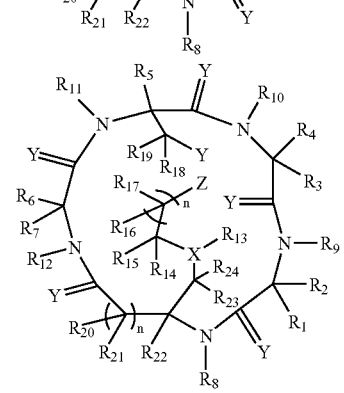

wherein X and Y includes independently a B, a C, a N, a O, a S, a P, or a Se, and R1-R24 and Z include independently one or more optionally substituted groups selected from a H, a B, a C, a N, a O, a S, a P, a Se, an lower alkyl, an alkoxy, an alkoxyalkyl, a hydroxy, a hydroxyalkyl, an alkenyl, an amino, an imino, a nitrate, an alkylamino, a dialkylamino, a nitro, a nitroso, an aryl, a biaryl, a polycyclic aromatic, an alkylaryl, an arylalkyl, an arylalkoxy, an arylalkylamino, a cycloalkyl, a bridged cycloalkyl, a cycloalkoxy, a cycloalkyl-alkyl, an arylthio, an alkylthio, an alkylsulfinyl, an alkylsulfonyl, an arylsulfonyl, an arylsulfinyl, a caboxamido, a carbamoyl, a hydroxamate, a carboxyl, a carbonyl, an alkoxycarbonyl, a halogen, a haloalkyl, a haloalkoxy, a heteroayl, a heterocyclic ring, an arylheterocyclic ring, a heterocyclic compound, an amido, an imido, a guanidino, a hydrazido, an aminoxy, an alkoxyamino, an urea, an alkylamido, a carboxylic ester, a thioether, a carboxylic acid, a phosphoryl group, a polycyclic aromatic and combinations thereof. And, n is 0, 1, 2, 3, 4, 5, 6, 7, etc.

BRIEF DESCRIPTION OF THE DRAWINGS

For a more complete understanding of the features and advantages of the present invention, reference is now made to the detailed description of the invention along with the accompanying figures and in which:

FIGS. 1A-1D are images of the structures of representative histone deacetylase inhibitors from the different structural classes;

FIGS. 9-11 are graphs of growth inhibition of prostate cancer cells by modified FK228 analogues of the present invention;

DETAILED DESCRIPTION OF THE INVENTION

Figure 2:
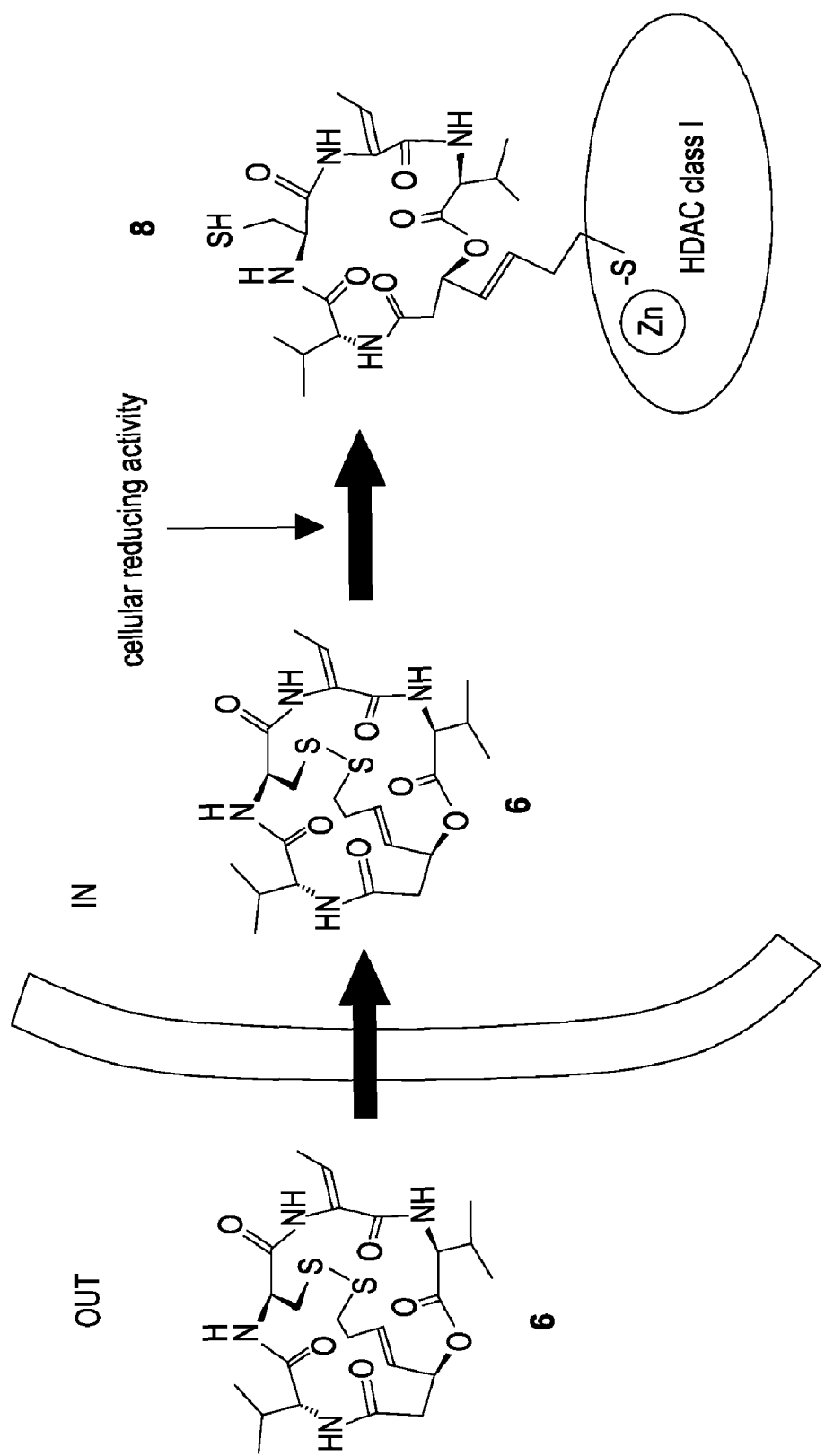
FIG. 2 is a schematic illustrating a model for inhibition of a cellular HDAC by FK228.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term depsipeptide is used interchangeably with the terms, FK228, and FR901228 to denote the naturally occurring cyclic peptide histone deacetylase inhibitor having the structure given as FK228.

As used herein, the term "Alkyl" denotes branched or unbranched hydrocarbon chains, having between about 1-20 carbons, with "lower Alkyl" denoting branched or unbranched hydrocarbon chains, having between about 1-10 carbons. Non-limiting examples include methyl, ethyl, propyl, n-propyl, isopropyl, butyl, n-butyl, sec-butyl, isobutyl, t-butyl, 1-methylpropyl, pentyl, isopentyl, sec-pentyl, 2-methylpentyl, hexyl, heptyl, octyl, nonyl, decyl, octa-decyl and so on. Alkyl includes cycloalkyl, such as cyclopropyl, cyclobutyl, cyclopentyl, and cyclohexyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, hydroxamate, alkyl, alkenyl, alkynyl, nitro, amino, alkoxy, amido, imino, imido, guanidino, hydrazido, aminoxy, alkoxyamino, urea, and the like to form alkyl groups such as trifluoro methyl, 3-hydroxyhexyl, 2-carboxypropyl, 2-fluoroethyl, carboxymethyl, cyanobutyl and the like.

As used herein, the term "Aryl" denotes a chain of carbon atoms which form at least one aromatic ring having between about 4-20 carbon atoms, such as phenyl, naphthyl, biphenyl, anthracenyl, pyrenyl, tetrahydronaphthyl, and so on, any of which may be optionally substituted. Aryl also includes arylalkyl groups such as benzyl, phenethyl, and phenylpropyl. Aryl includes a ring system containing an optionally substituted 5 or 6-membered carbocyclic aromatic ring, said system may be bicyclic, polycyclic, bridge, and/or fused. The system may include rings that are aromatic, or partially or completely saturated. Examples of ring systems include phenyl, naphtyl, biphenyl, anthracenyl, pyrenyl, imidazolyl, triazolyl, tetraazolyl, oxazolyl, thiophenyl, pyridyl, pyrrolyl, furanyl, quinolyl, quinolinyl, indenyl, pentalenyl, 1,4-dihydronaphthyl, indanyl, benzimidazolyl, benzothiophenyl, indolyl, benzofuranyl, isoquinolinyl, and so on. The group may be substituted with one or more functional groups which are attached commonly to such chains, such as boronyl, hydroxyl, bromo, fluoro, chloro, iodo, mercapto or thio, cyano, cyanoamido, alkoxy, alkylthio, heterocycle, aryl, heteroaryl, carboxyl, carbalkoyl, carboxamidyl, alkoxycarbonyl, carbamyl, hydroxamate, alkyl, alkenyl, alkynyl, nitro, amino, alkoxy, amido, imino, imido, guanidino, hydrazido, aminoxy, alkoxyamino, urea, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, aminophenyl, amidophenyl, thiazolylphenyl, oxazolylphenyl, imidazolylphenyl, imidazolylmethylphenyl, and the like.

As used herein, the term "Alkenyl" includes optionally substituted straight chain and branched hydrocarbons having between about 1-50 carbons as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbons having a mixture of double bonds and triple bonds, such as 2-penten-4-ynyl, are grouped as alkynyls herein. Alkenyl includes cycloalkenyl. Cis and trans or (E) and (Z) forms are included within the invention. These groups can be optionally substituted with one or more functional groups which are attached commonly to such chains, such as, boronyl, hydroxyl, bromo, fluoro, chloro, iodo, mercapto or thio, cyano, alkoxy, alkylthio, heterocyclyl, aryl, heteroaryl, carboxyl, carbalkoyl, carboxamidyl, alkoxycarbonyl, carbamoyl, hydroxamate, alkyl, alkenyl, alkynyl, nitro, amino, alkoxy, amido, imino, imido, guanidino, hydrazido, aminoxy, alkoxyamino, urea, and the like to form alkyl groups such as trifluoro methyl, 3-hydroxyhexyl, 2-carboxypropyl, 2-fluoroethyl, carboxymethyl, cyanobutyl and the like.

As used herein, the term "Alkynyl" includes optionally substituted straight chain and branched hydrocarbons having between about 1-50 carbons as above with at least one carbon-carbon triple bond (sp). Alkynyls include ethynyl, propynyls, butynyls, and pentynyls. Hydrocarbons having a mixture of double bonds and triple bonds, such as 2-penten-4-ynyl, are grouped as alkynyls herein. Alkynyl does not include cycloalkynyl. These groups can be optionally substituted with one or more functional groups which are attached commonly to such chains, such as, boronyl, hydroxyl, bromo, fluoro, chloro, iodo, mercapto or thio, cyano, alkoxy, alkylthio, heterocyclyl, aryl, heteroaryl, carboxyl, carbalkoyl, carboxamidyl, alkoxycarbonyl, carbamoyl, hydroxamate, alkyl, alkenyl, alkynyl, nitro, amino, alkoxy, amido, imino, imido, guanidino, hydrazido, aminoxy, alkoxyamino, urea, and the like to form alkyl groups such as trifluoro methyl, 3-hydroxyhexyl, 2-carboxypropyl, 2-fluoroethyl, carboxymethyl, cyanobutyl and the like.

As used herein, the term "Alkoxy" includes an optionally substituted straight chain or branched alkyl group having between about 1-25 carbons with a terminal oxygen linking the alkyl group to the rest of the molecule. Alkoxy includes methoxy, ethoxy, propoxy, isopropoxy, butoxy, t-butoxy, pentoxy and so on. Alkyoxy also includes any substituted alkyl group connected by an ether linkage, such as aminobutoxy, carboxyethoxy, hydroxyethoxy and so on. "Aminoalkyl", "thioalkyl", and "sulfonylalkyl" are analogous to alkoxy, replacing the terminal oxygen atom of alkoxy with, respectively, NH (or NR), S, Se, and $SO_2$. Heteroalkyl includes alkoxy, aminoalkyl, thioalkyl, selenoalkyl, and so on.

As used herein, the terms "cancer" means an increase in the number of abnormal cells derived from a given normal tissue or any clinical definition. In addition, it may involve the invasion of adjacent or non-adjacent tissues and/or the lymphatic or blood-borne spread of malignant cells to other sites and/or regional lymph nodes. Furthermore, the term also encompasses hyperplasia, precancerous cells and minor preneoplastic changes.

As used herein, the term "preventing cancer" means to inhibit the transformation of a cell into an abnormal cell by a carcinogenic agent or agents and/or to inhibit the accumulation of cells expressing cancer-specific genes to a number that creates one or more clinical symptoms associated with cancer.

As used herein, the terms "treating cancer" and "treatment of cancer" mean to at least partially inhibit the replication of cancer cells, to inhibit the spread of cancer, to decrease tumor size, to lessen or reduce the number of cancerous cells in the body, to ameliorate or alleviate the symptoms of the disease caused by the cancer. The treatment is considered therapeutic if there is a decrease in mortality and/or morbidity.

As used herein, the term "pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

The present invention provides a potent histone deacetylase inhibitor for use in the treatment of various conditions including but not limited to cancer and sickle cell disease. Some histone deacetylase inhibitors are in phase I/II clinical trials as anti-cancer agents; however, several compounds which have shown potent anti-cancer activity in vitro, are found to be associated with intolerable toxicity in vivo. The high toxicity presumably results from non-selective inhibition of vital histone deacetylases in cells and brings in significant concern of employing histone deacetylase inhibitors for the chronic treatment.

The present inventor recognized that a potent and selective histone deacetylase inhibitor with a lower cellular toxicity is needed for treatment (e.g., of cancer and sickle cell disease). The present inventor recognized that the identification of novel structural analogues of depsipeptide (also known as FK228), the most potent histone deacetylase inhibitor as a treatment for various diseases.

The present inventor recognized that despite its high potency in vitro and in vivo, the structure of depsipeptide has not been explored at all to pursue greater activity or selectivity toward different histone deacetylases because of several synthetic challenges associated with its privileged structure. Therefore, the present invention provides an alternative core structure for depsipeptide to provide methods of synthesis with high efficiency and retained high potency toward histone deacetylases, while having a significantly reduced toxicity to cells.

Several classes of histone deacetylases inhibitors have been shown to induce fetal hemoglobin (HbF) in erythroid cells. DNA exists in cells in the form of chromatin which functions as a dynamic scaffold to regulate various nuclear processes including DNA transcription, replication, repair, mitosis and apoptosis.[39,40] The basic building block of chromatin is the nucleosome, a structure consisting of an octamer of four core histone protein around which 147 bp of DNA is wrapped.[41] The histone proteins H1, H2A, H2B, H3 and H4 each contain a high proportion of positively charged arginine and lysine residues, which increases their binding affinity to negatively charge DNA. Chromatin and DNA are the prime targets of epigenetic changes in gene expression that influence clinical phenotype without changes in primary DNA sequences (or genotype). The epigenetic changes that produce histone modifications and DNA methylation are intimately connected.[42]

Each histone protein contains an N-terminal tail domain ranging from 16 to 44 amino acids long that extends out of the nucleosome core. Histone tails are essential for higher-order folding of chromatin fibers and provide binding sites for non-histone regulatory proteins.[43,44] Histone-specific post-translational modifications including acetylation, methylation, phosphorylation, ubiquitylation, sumoylation[45] and ADP-ribosylation[46] targeted mainly to histones H3 and H4; the enzymes responsible for these modifications have been characterized; they include histone acetyltransferases (HATs), histone methyltransferases (HMTs), ubiquitin ligases and kinases. The enzymes that remove histone modifications are histone deacetylases (HDACs), demethylases, deubiquitinases and phosphatases.[49-51]

Histones are regarded as integral and dynamic components of the gene transcriptional machinery.[52-54] Acetylation of specific lysine residues on the H3 tail has been associated with active chromatin regions.[55,56] When the acetyl group is removed, HDAC-associated gene repression occurs after the positive charge has been restored, thereby increasing interactions with DNA. The balance between histone acetylation and deacetylation is catalyzed by HATs and HDACs respectively. Phylogenic analyses have been used to subdivided human histone deacetylases into four[57] distinct classes including, Class I histone deacetylases, related to yeast Rpd3 consisting of HDAC1, HDAC2, HDAC3 and HDAC8, and Class II histone deacetylases related to yeast Hda1 including HDAC4, HDAC5, HDAC6, HDAC7, HDAC9, and HDAC10. The Class III histone deacetylases are NAD-dependant and related to the yeast silencing protein Sir2 and the newly isolated structurally unique HDAC11 has been placed in Class IV.[58] Less is known about histone methylation[59,60] however, mono-, di-, and tri-methylated lysine residues have been observed on histone H3 and H4 at six lysine residues.[61] At least three protein motifs—the chromodomain,[62-64] tudor domain[65,66] and WD40-repeat-domain[67] are capable of interacting with methylated lysine residues. Methylation of histone H3, lysine 4 (H3K4), and H3K9, has been linked to active gene transcription.[68-71]

Figure 8:
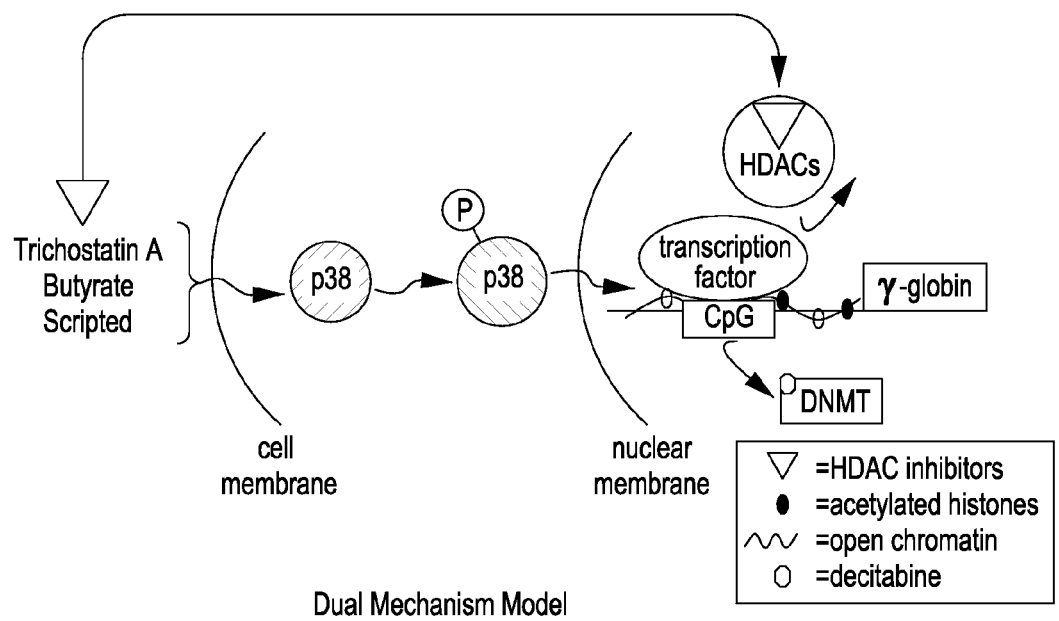
FIG. 8 is a schematic of a model for γ-globin gene activation and fetal hemoglobin (HbF) induction by histone deacetylase inhibitors in erythroid cells.

All events that occur within chromatin must be initiated and regulated by DNA-regulatory proteins. Histone deacetylases have no DNA binding activity therefore any DNA-binding protein that targets histone deacetylases to DNA can alter gene transcription. The activity of histone deacetylases can be separated into two categories, enzymatic activity (i.e., the ability to deacetylate proteins), and functional activity (i.e., the ability to regulate transcription). The tails of the core histones are covalently modified[72-74] through the action of HAT enzymes. After that ATP-dependent chromatin remodeling factors alter histone-DNA interactions such that nucleosomal DNA becomes more accessible to DNA-binding proteins.[75,76] A similar model for γ-globin gene activation and fetal hemoglobin (HbF) induction by histone deacetylases inhibitors in erythroid cells as shown in FIG. 8.[77]

In addition, several histone deacetylases exist as components in large multi-protein complexes, e.g., HDAC1 and HDAC2 exist together in the Sin3, NuRD/NRD/Mi2, and CoREST repressor complexes.[78-84] Sin3 and NuRD complexes share a core of four proteins: HDAC1, HDAC2, RbAp46, and RbAp48. Perhaps the best example of histone deacetylase regulation by protein-protein interaction emanated from studies of HDAC3. The silencing mediator of retinoid and thyroid receptor (SMRT) and nuclear receptor co-repressor (N-CoR), function as platforms for the recruitment of histone deacetylases.[85,86] The three proteins that activate Class I histone deacetylase activities MTA2, CoREST, and SMRT/N-CoR all possess a putative DNA binding domain present in a number of transcriptional regulators.[87]

Posttranslational histone modifications at the ε-amino group of histone tails contributes to gene regulation.[88-90] The histone deacetylases also play a dynamic role in regulating cell cycle progression. The importance of histone acetylation to the process of carcinogenesis can be seen from the fusion genes (e.g. PML/RARα, PLZF/RARα, and AML1/ETO), found in acute myeloid leukemia. Gene transcription is altered by recruiting histone deacetylases and inhibition of differentiation of affected hematopoietic cells.[91-93] Inappropriate transcriptional repression mediated by Class I and II histone deacetylases can be found in many cancers.[94] Thus, histone deacetylases have been developed as promising anticancer therapeutics and a number of such compounds have been reported in recent literature.[95] There has also been great interest in histone deacetylases as HbF inducers to treat sickle cell disease (SCD). Several structurally diverse classes of natural and synthetic histone deacetylases inhibitors are known to bind histone deacetylases and block histone deacetylation.[96]

The presence of histone hyperacetylation and altered patterns of transcription factors bound to the γ-globin promoters in individuals treated with arginine butyrate, highlight the importance of chromatin remodeling in vivo to produce HbF induction by histone deacetylases inhibitors.[137] Selective fatty acids induce HbF including butyrate (NaB),[122,123] phenylbutyrate,[103] phenylacetic,[102] and phenylalkyl acids,[138-140] however most are rapidly metabolized making intravenous administration the most effective route. The ability of butyrate to activate γ-globin in humans and ameliorate the symptoms of SCD has been shown clinically.[122,123] Mechanistically, through histone acetylation the histone deacetylases inhibitors promote an open chromatin structure and access to DNA binding sites. Specific cis-active butyrate response elements (BREs) have been demonstrated in several genes stimulated by NaB.[141-143] Increased DNA accessibility for effector molecules that bind BREs in the γ-promoter is produced by histone hyperacetylation. SAHA and Scriptaid induce HbF synthesis in murine and human erythroleukemia cell lines[77,146,147] and in vivo.[77] Hydroxyurea (HU),[148] valproate,[149] NaB, and TSA,[100,101] stimulate γ-globin expression via p38 MAPK signaling. It is known that NaB induces erythroid differentiation through Janus kinase 2/Stat5 signaling in mouse erythroleukemia cells.[99]

Post-translational modifications at the ε-amino group of histone tails contributes to gene regulation.[48-50] The histone deacetylases also play a dynamic role in regulating cell cycle progression. Inappropriate transcriptional repression mediated by Class I and II histone deacetylases can be found in many cancers.[51] The present invention provides histone deacetylase inhibitors as anticancer therapeutics. In addition, the present invention includes the use of histone deacetylase inhibitors as HbF inducers to treat SCD.

FIG. 1 is an illustration of the structure of the structurally diverse classes of natural and synthetic histone deacetylase inhibitors known to bind histone deacetylases and block histone deacetylation[53]. FIG. 1A includes short-chain fatty acids (sodium butyrate (NaB), valproate, phenylbutyrate, proprionte, etc.). FIG. 1B includes benzamides (MS-275, CI-994, etc.). FIG. 1C includes non-cyclic and cyclic hydroxamates such as SAHA (suberoylanilide hydroxamic acid), TSA (Trichostatin A), and oxamflatin. FIG. 1D includes cyclic peptides (depsipeptide (FK228), trapoxin, apicidin, etc.).

The first HDAC inhibitor reported was NaB[54-55], which has pleiotropic effects on several target genes. NaB induces differentiation in mouse erythroleukemia cells via Stat5 signaling (56) and HbF synthesis through p38 mitogen activated protein kinase signaling.[56-58] Other fatty acids HDAC inhibitors such as phenylacetate, phenylbutyrate and proprionate[59-61] have been shown to induce HbF in erythroid progenitors. These findings serve as the basis for widespread research efforts to develop histone deacetylase inhibitors as therapeutic agents for SCD.

Of the hydroxamic acid derivatives, the prototype TSA was isolated from *Streptomyces hygroscopicus* and shown to be a potent histone deacetylase inhibitor.[62-63] It interacts with a divalent zinc-binding motif in the binding pocket of class I and II histone deacetylases.[64] Other histone deacetylase inhibitors in this hydroxamic acid class include the second generation analogues of TSA. The most widely studied compounds are SAHA and Scriptaid. SAHA targets HDAC 1, 3, and 4 and inhibits prostate cancer cell growth in vitro and in vivo.[66-67] Recently, it was demonstrated that SAHA and Scriptaid induce HbF synthesis superior to NaB and TSA in erythroid cells and β-YAC transgenic mice.[47]

The fourth class of HDAC inhibitors is cyclic peptides, Trapoxins A (TPX A) and TPX B isolated from a fungus, *Helicoma ambients*.[68] TPX A is a potent irreversible histone deacetylase inhibitor, suggesting that it covalently binds to histone deacetylases via the epoxide functional group.[69] Cyclic tetrapeptides containing hydroxamic acid functionality (CHAPs) are also prepared as hybrid of TSA and TPX.[70] The hydroxamic acid group is attached to the cyclic peptide core instead of the epoxyketone found in TPX, and a number of analogues have been made by substituting amino acid residues and their chirality.[71-73] Among the derivatives tested, CHAP31 was found to be the most potent histone deacetylase inhibitor with an $IC_{50}$ of 3.32 nM and more stable compared to TSA. The general cytotoxic action of histone deacetylase inhibitors has been studied intensively. Modulation of genes related to the cell cycle and apoptosis are considered to be responsible for HDACI-induced cytotoxicity.[74-76] Among this diverse group of compounds, butyrate, phenylbutyrate, SAHA, FK228, MS-275, CI-994, and valproate among others are already in phase I/II clinical trials in cancer[77] and sickle cell patients.[77-79]

FIG. 2 is a schematic of the uptake of depsipeptide. The naturally occurring cyclic peptide HDAC inhibitor, depsipeptide, was isolated from *Chromobacterium violaceum*[80]. It has a unique bicyclic structure and is a prodrug 6, which is stable, inactive and hydrophobic. The prodrug 6 becomes activated by reduction of the disulfide bond by glutathione to produce active form (redFK) 8 after uptake into cells.[81] The active form (redFK) 8 becomes hydrophilic, less stable and active. The reduced sulfhydryl group interacts strongly with the zinc ion at the active site of the enzyme.[82] The half-life of depsipeptide 6 and redFK 8 is >12 and 0.54 hours respectively in growth medium and inhibits tumor proliferation in vitro and in vivo at nanomolar concentrations.[83-85] Mechanisms for how depsipeptide induces apoptosis in leukemic cells involve activation of tumor necrosis factor-α in HL-60 and K562 cells.[86]

The presence of histone hyperacetylation and altered patterns of transcription factors bound to the γ-globin promoters in individuals treated with arginine butyrate, highlight the importance of chromatin remodeling in vivo to produce HbF induction by histone deacetylase inhibitors.[88] Selective fatty acids induce HbF including butyrate[89] and phenylbutyrate[60], however most are rapidly metabolized making intravenous administration the most effective route. The ability of butyrate to activate γ-globin in humans and ameliorate the symptoms of SCD has been shown clinically.[89-90] Mechanistically, through histone acetylation the histone deacetylase inhibitors promote an open chromatin structure and access to DNA binding sites. Specific cis-active butyrate response elements (BREs) have been demonstrated in several genes stimulated by NaB.[91-93] The dual mechanism model proposed whereby a histone deacetylase inhibitor mediates γ-gene reactivation[47]. Increased DNA accessibility for effector molecules that bind BREs in the γ-promoter is produced by histone hyperacetylation. SAHA and Scriptaid have been shown by Pace and others to induce HbF synthesis in murine and human erythroleukemia cell lines and in vivo.[47,96-97]

Figure 3A:
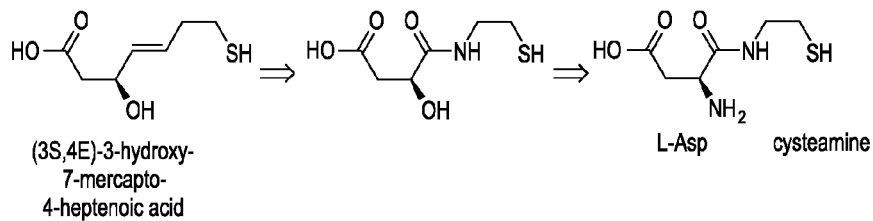
FIG. 3A is an image of the structure of a building block employed in FK228 that associates with high synthetic difficulty and a schematic diagram of its conversion to a structure which can be readily assembled, a conjugate of an amino acid and an amino thiol.

FIG. 3A is an image of the structure of a building block employed in the histone deacetylase inhibitor, depsipeptide, which is a bicyclic depsipeptide that almost exclusively consists of unnatural amino acids, D-valine, D-cysteine and (Z)-dehydrobutyrine as well as (3S,4E)-3-hydroxy-7-mercapto-4-heptenoic acid which is a key component to form the highly constrained bicyclic structure. The high content of the unnatural amino acids and the constrained bicyclic structure make it extremely stable in physiological condition, and its high hydrophobicity makes it easy to penetrate through cell membrane to approach the target proteins, histone deacetylases. Isolated from *Chromobacterium violaceum* in 1994,[80] Li and coworkers first reported its total synthesis in 1996[98] and suggested a synthetic route with moderate yield (19 steps and 18% overall yield).

Figure 3B:
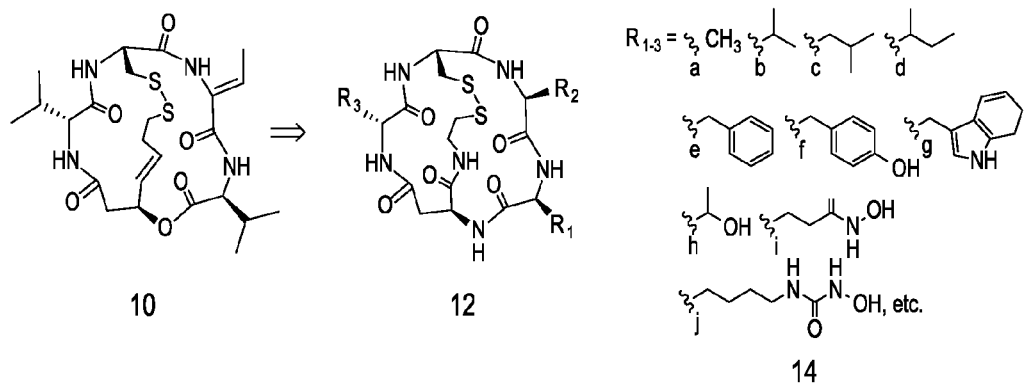
FIG. 3B is an image of the structure of FK228 compared to the modified histone deacetylase inhibitor core structure of the present invention.

FIG. 3B is an image of the structure of the histone deacetylase inhibitor, depsipeptide 10 compared to the modified histone deacetylase inhibitor core structure 12 of the present invention. The modified histone deacetylase inhibitor core structure 12 of the present invention may be modified by the substitution of one or more functional groups 14.

Figure 3C:
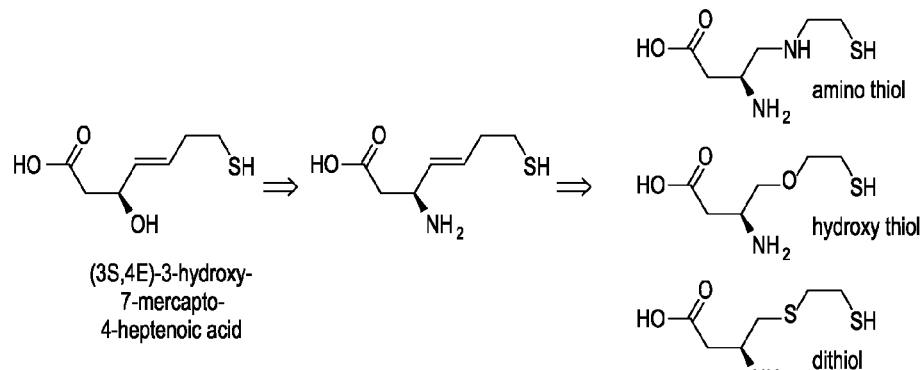
FIG. 3C is an image of the structure of a building block employed in FK228 that associates with high synthetic difficulty and a schematic diagram of its conversion to a structure which can be readily assembled, a conjugate of an amino acid and an amino thiol, a hydroxy thiol, or a dithiol.
Figure 3D:
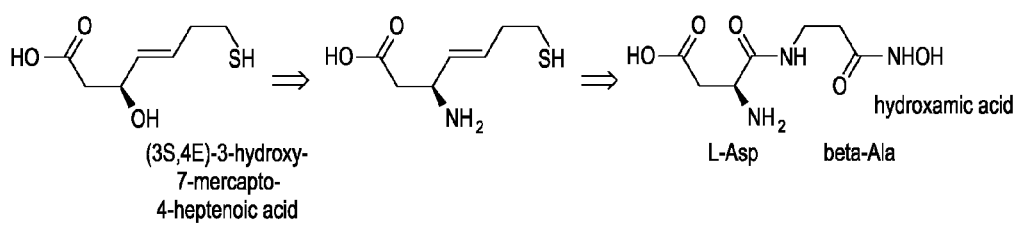
FIG. 3D is an image of the structure of a building block employed in FK228 that associates with high synthetic difficulty and a schematic diagram of its conversion to a structure which can be readily assembled, a conjugate of an amino acid and a hydroxamic acid.
Figure 3E:
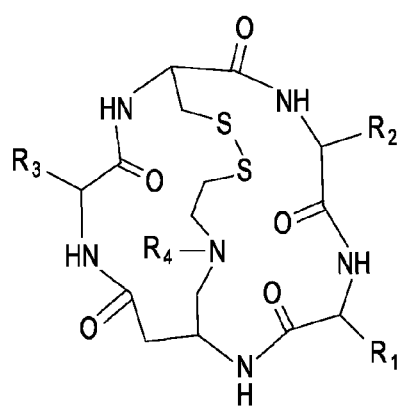
FIGS. 3E-3H are images of the modified histone deacetylase inhibitor core structures of the present invention comprising an amino acid conjugate which constitutes an amino thiol, a hydroxy thiol, a dithiol, or a hydroxamic acid.
Figure 3F:
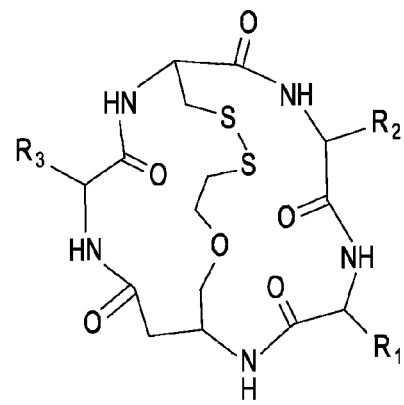
Figure 3G:
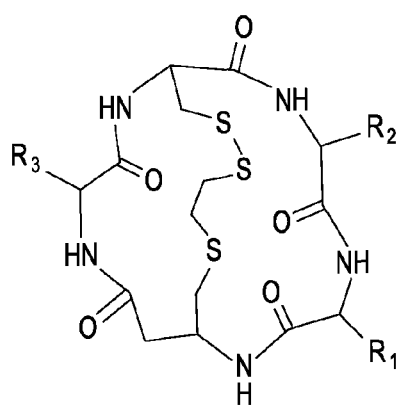
Figure 3H:
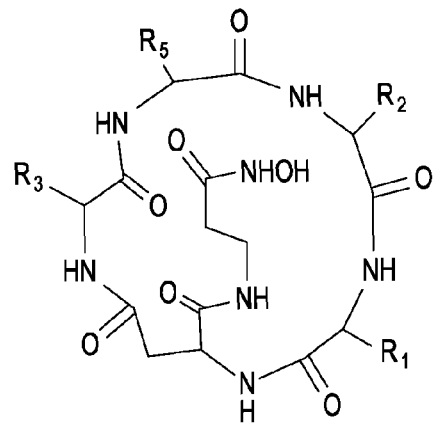

FIGS. 3C and 3D are images of the structures that can be used to replace (3S,4E) -3-hydroxy-7-mercapto-4-heptenoic acid to construct modified histone deacetylases inhibitor core structures illustrated in FIG. 3E-3H.

Due to its challenging and non-trivial synthesis, depsipeptide has not been modified or derivatized at all despite its exceptionally high in vitro and in vivo activity (inhibition of tumor growth and induction of γ-globin in nanomolar concentration), while other HDAC inhibitors which can easily be prepared have been intensively explored. The three principle synthetic challenges associated with its synthesis are (1) the asymmetric synthesis of the (3S,4E)-3-hydroxy-7-mercapto-4-heptenoic acid, (2) the macrolactonization to form the 16-membered cyclic depsipeptide, and (3) the oxidation of thiols to form the 15-membered ring.[98] These synthetic difficulties can be worked around if only a small number of derivatives are to be synthesized, but remain as the main obstacles to explore highly diverse structures. In general, synthesis of a large number of derivatives is often necessary in drug discovery since there is always the possibility of trial and error in pursuit of higher potency and selectivity. For this reason, solid-phase synthesis is an efficient method since it can be easily adapted to a high-throughput format (including parallel synthesis) in order to achieve high molecular diversity. Therefore, synthetic efficiency, such as higher yields, easy derivatization, readily available starting materials and synthetic chemistries suitable for automation, should be considered.

Figure 4:
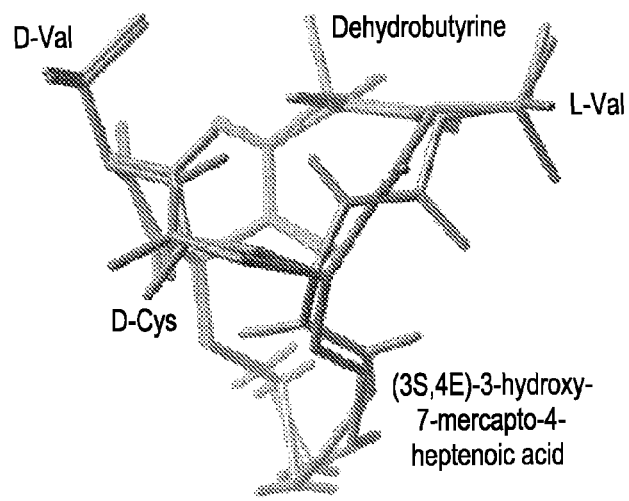
FIG. 4 is an image of a model of the superimposed structures of FK228 and a modified histone deacetylase inhibitor core structure of the present invention.

FIG. 4 is an image of a model of the superimposed structures of depsipeptide and the modified histone deacetylase inhibitor core structure 12. For the facile synthesis of the modified FK228 analogues of the present invention, the most synthetically challenging moiety the hydroxy-mercapto-heptenoic acid was converted into a structure, which can be prepared with significantly less effort but still with the capability to hold the same structure required for biological activity as seen in FIG. 3A. First, the trans-double bond in the heptenoic acid was changed to an amide functional group. In many cases, amide bonds in peptides have been successfully replaced by trans-double bonds for the development of peptidomimetics due to its structural rigidity and capability to present two alkyl groups on the opposite sides.[99-100] In this case, the amide was used as a structural isostere of the trans-double bond. The ester group to form the depsipeptide was replaced by an amide for the facile macrocyclization which can provide higher synthetic yield as well as increase stability in vivo. These two simple conversions transformed the synthetically challenging (3S,4E)-3-hydroxy-7-mercapto-4-heptenoic acid into a structure which can be prepared with a L-aspartic acid and cysteamine and provided a tremendously efficient synthetic route to prepare the modified FK228 analogues of the present invention.

To assure that the modifications described above do not alter the structure of the native depsipeptide, the structure of the modified histone deacetylase inhibitor core structure containing L-aspartic acid and cysteamine was studied by molecular modeling. The conformational search was carried out with MacroModel (version 9.1, Schrodinger)[101], and Monte Carlo conformational search (e.g., 5,000 steps) was carried out using united atom AMBER force field[102] implemented into the MacroModel program. The conformations saved after the Monte Carlo conformational search were energy minimized using the AMBER force field with conjugate gradient. The structure of the modified histone deacetylase inhibitor core structure is almost identical to the structure of the native depsipeptide (RMSD=0.20 Å), indicating that the structural modification does not disturb the overall conformation of the molecule.

Figure 5:
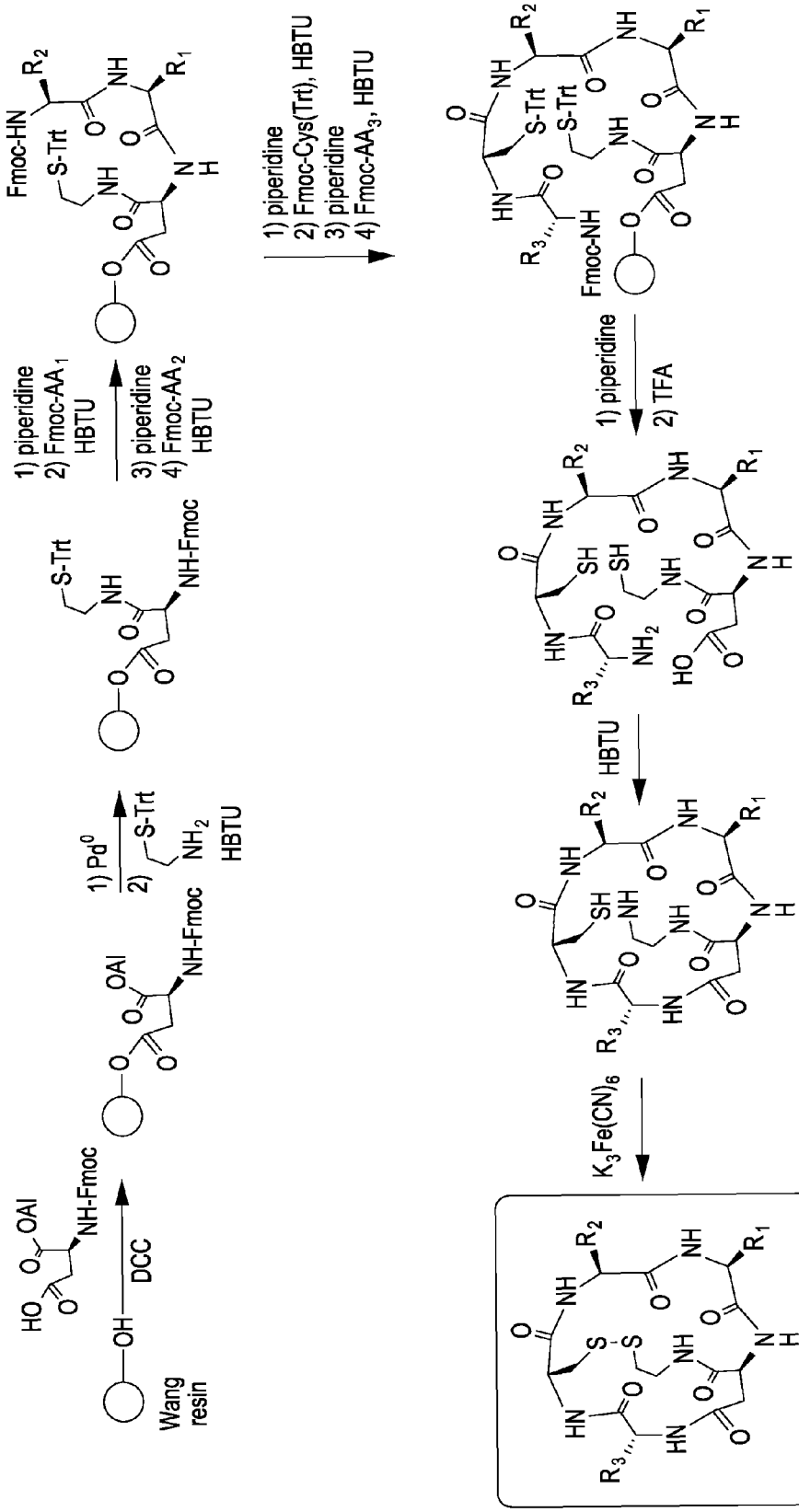
FIG. 5 is a schematic of one of the synthetic routes to make the modified FK228 analogues of the present invention.

FIG. 5 is a schematic of one of the synthetic routes to make the modified FK228 analogues. Since two amino acids (D-cysteine and the L-aspartic acid) are required to form the unique bicyclic structure, the remaining three amino acids (D- and L-valines and dehydrobutyrine) in the structure of the modified FK228 derivatives can be varied to produce a number of modified FK228 derivatives. In order to preserve the privileged bicyclic structure of the native depsipeptide, each amino acid residue was replaced with an amino acid in the same stereochemistry, but this does not limit further derivatizations with amino acids in opposite chirality in future. In other words, in the beginning the D-Val was substituted with a D-amino acid, while the L-Val with a L-amino acid. However, the dehydrobutyrine was substituted with either a L- or D-amino acid due to the absence of stereochemistry at its α-carbon.

The synthesis of several modified FK228 analogues were carried out using standard Fmoc chemistry of solid-phase peptide synthesis technique. To hydroxymethyl-containing polystyrene resin used as a polymer support (e.g., Wang resin),[103] Fmoc-Asp-OAl was anchored. After the removal of an allyl protection group using Pd⁰, Trt-protected cysteamine was coupled to the Fmoc-Asp. Then, 4 amino acids were coupled to the Asp-cysteamine, and the linear and reduced intermediate 16 was released from the resin using TFA. The monocyclic peptide 16 was prepared by the formation of lactam bond using HBTU[104] and the reduced monocyclic peptide 18 was oxidized with $K_3Fe(CN)_6$ in solution to obtain modified FK228 derivatives (20). All of the reactions described above proceeded with extremely high yields and a number of analogues were prepared with high synthetic efficiency. The present invention provides a preparation of compounds in as little as a week with yields of greater than 80% and with a purity of greater than 85%, in comparison the synthesis of native depsipeptide has about a 18% overall yield in much more synthetic steps.

The synthesized modified FK228 analogues of the present invention were assessed to examine their capability to induce γ-globin expression. K562 cells were treated with the synthesized modified FK228 analogues at various concentrations (e.g., between about 0.01 nM and about 10 μM) for about 48 hours and expression of γ-globin was determined by real-time PCR as well as checking cell viability. It is quite promising that most of the modified FK228 analogues of the present invention were found to non-toxic to cells up to about 10 μM, showing greater than 90% cell viability, while TSA a potent histone deacetylase inhibitor with less selectivity, was found to be toxic to cells with only about 30-40% viability even at substantially lower concentration of about 0.3 μM.

As the modified FK228 analogues of the present invention has similar physico-chemical properties as the native depsipeptide, the modified FK228 analogues of the present invention appear to penetrate cell membrane easily and interact with histone deacetylases within the cells showing a range of γ-globin expression level.

Figure 6A:
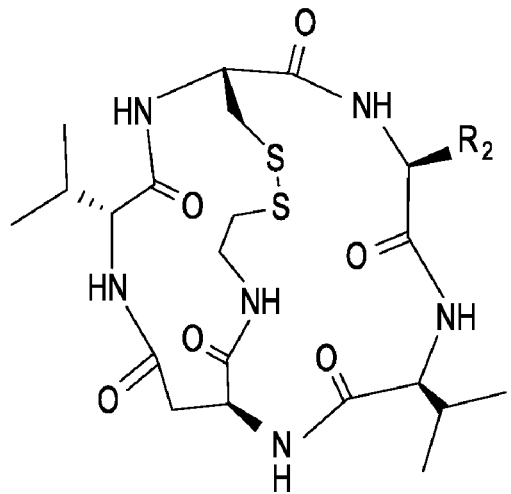
FIG. 6A is the structure of the modified FK228 analogues seen in the graph of FIG. 6B.
Figure 6B:
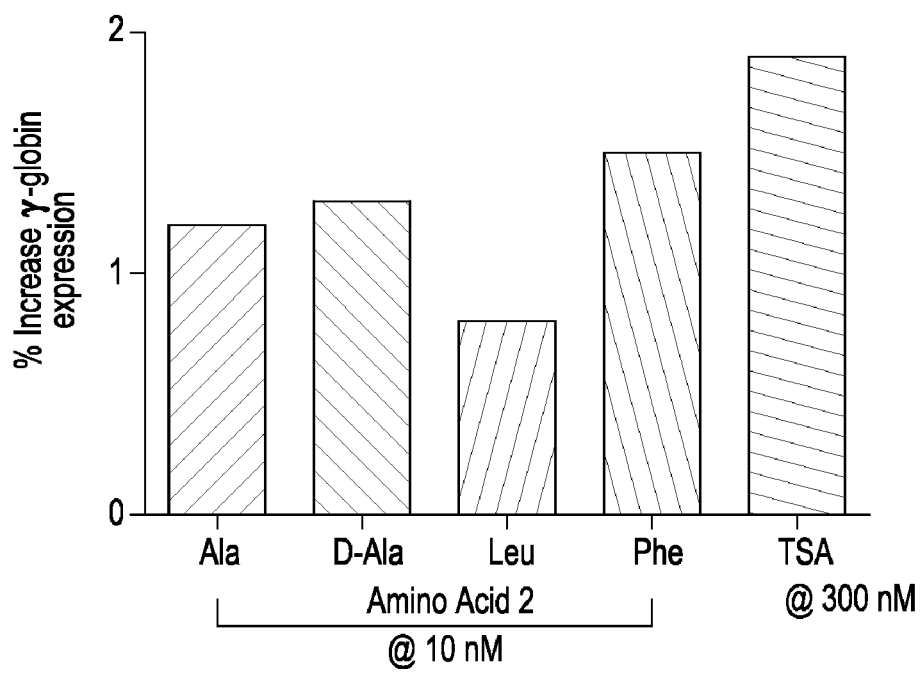

FIG. 6A is the structure of the modified FK228 derivatives of the present invention. FIG. 6B is a graph of the increase of γ-globin expression by the modified FK228 analogues of FIG. 6A of the present invention. The activity of the modified FK228 derivatives of the present invention were analyzed at 10 nM whereas TSA at 300 nM. This indicates that the structural modification in the modified FK228 analogues did not disturb their capability to interact with histone deacetylases. Furthermore, the modified FK228 analogues of the present invention show different activity depending on their specific structure. The present invention provides the modified FK228 analogues that are potent, selective and less toxic histone deacetylase inhibitors. In addition, the modified FK228 analogues of the present invention can be used to induce γ-globin expression. The modified FK228 analogues of the present invention were not possible until the facile synthetic method was developed by the present inventor.

The present invention provides a method of making structurally diverse modified FK228 analogues that have higher potency and selectivity toward different histone deacetylases. Histone deacetylases play an important role in gene transcription and histone deacetylase inhibitors induce cell differentiation and inhibit cell growth in tumor cells as well as induction of γ-globin expression which is highly favorable to treat SCD. Histone deacetylases are typically classified into 4 class, and class I HDACs include HDAC1, HDAC2, HDAC3, and HDAC8 while class II HDACs are HDAC4, HDAC5, HDAC6, HDAC7, HDAC9, and HDAC10. Each member of the histone deacetylase family is a component of a complex playing a distinct role in gene expression.[105] For example, retinoblastoma tumor suppressor protein is associated with a large protein complex containing HDAC1 and E2F transcription factor[106] while HDAC4 and HDAC5 are associated specifically with myocyte enhancer factor MEF2A and repress MEF2A-dependent transcription.[107]

Histone deacetylases selectively regulate specific genes, it is obvious that the selective inhibition of specific histone deacetylases over others is highly desirable and more likely to yield specific and non-toxic drugs.[105,108] When 3D models were built using the X-ray crystal structure of HDAC8[109-110], they clearly reveal that all of the class I histone deacetylases share the same tube-like, 11 Å deep channel at the bottom of which a catalytic Zn ion is despite some difference in sequence homology.[105] It appears that non-specific histone deacetylase inhibitors like TSA and SAHA interact with the zinc ion through this narrow channel. In addition, there is a 14 Å long internal cavity adjacent to the $Zn^{2+}$ binding site, serving as a secondary binding site. Although the role of this internal cavity is not clearly elucidated, it showed more sequence diversity between histone deacetylases compared to the 11 Å deep channel. This structural examination of histone deacetylases suggests that selectivity between histone deacetylases may be achieved through the interactions between histone deacetylase inhibitors and these binding pockets.

While depsipeptide, the most potent histone deacetylase inhibitor, uses its free sulfhydryl group to interact with the catalytic zinc ion upon reduction inside cells by glutathione, it possesses other amino acid residues to occupy a secondary binding pocket. Thus, the high selectivity toward different histone deacetylases (between or within classes) can be achieved by screening structurally diverse modified FK228 analogues of the present invention. However, until the present invention, the structure of depsipeptide has not been varied due to several synthetic challenges that could not be overcome.

Although the synthetic scheme described in FIG. 5 can produce the modified FK228 analogues with high yield and purity, it can be only used to prepare structures with hydrophobic amino acids such as Ala, Val, Ile, Leu, Phe, Met, Pro, and etc. Also, it employs both solid-phase synthesis of linear and reduced intermediates and solution-phase cyclizations, which can be a bottle-neck if a large number of compounds are to be synthesized. Therefore, the present invention also provides a method of making the modified FK228 analogues using any amino acids (e.g., Lys, Asp, unnatural amino acids, and etc.) and optionally all steps can be carried out in solid-phase to increase synthetic efficiency.

Figure 7:
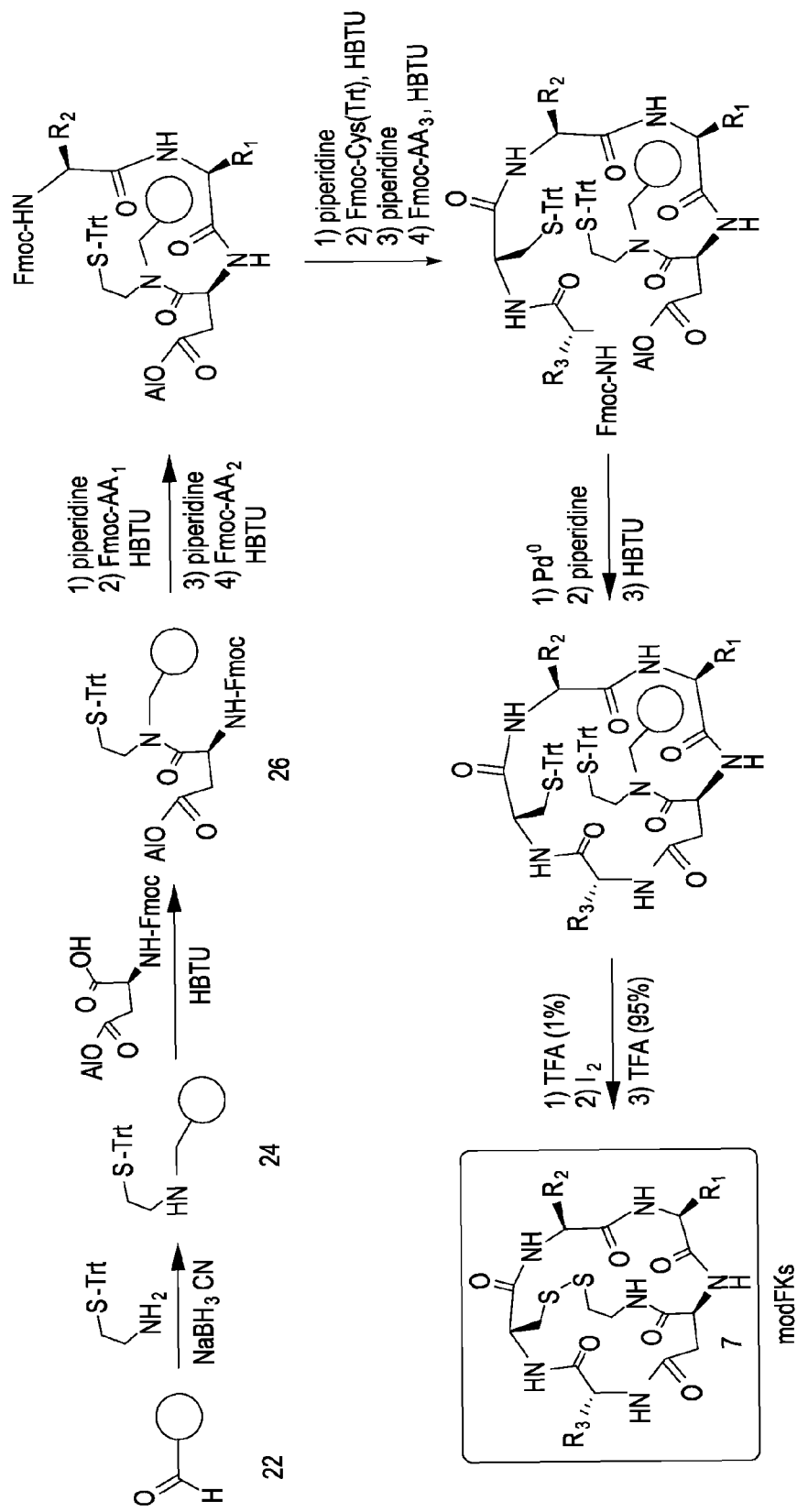
FIG. 7 is a schematic of one of the synthetic routes to make the modified FK228 analogues of the present invention using solid-phase synthesis techniques.

FIG. 7 is a scheme of the synthetic route to make the modified FK228 analogues of the present invention using aminomethyl-containing polystyrene resin as a polymer support and backbone amide linker (BAL) 22. As FIG. 7 shows, after BAL is coupled using a coupling reagent, HBTU, reductive amination reaction is carried out using Trt-protected cysteamine and $NaBH_3CN$. To the secondary amine 24 Fmoc-Asp-OAl is coupled, and the remaining amino acids are coupled using standard Fmoc chemistry of solid-phase peptide synthesis. Then, the allyl group is removed by using $Pd^0$, and the lactam bond is created to produce a monocyclic reduced intermediate 26, which is still anchored to the resin. The trityl protection groups on sulfhydryl groups are removed by TFA treatment (1% in DCM), and the peptide is oxidized by $I_2$ to result in a bicyclic modified FK228 analogues of the present invention. The final peptide is released from the resin by TFA treatment (>95% in concentration) with the simultaneous deprotection of all acid-labile protection groups used to protect reactive functional groups on Lys, Arg, Asp, Glu, Ser, Thr, Tyr, Trp, His, Asn, Glu, Cys, and unnatural amino acids. The synthesized modified FK228 analogues of the present invention can be easily purified by reverse-phase HPLC using an autosampler and a fractional collected equipped in a HPLC system.

Each of the 3 amino acid residues (2 L-amino acid and 1 D-amino acid) have been varied by incorporating L- or D-forms of aliphatic amino acids (e.g., Ala, Val, Leu, Ile, Pro), aromatic amino acids (e.g., Phe, Tyr, Trp, His), acidic amino acids (e.g., Asp, Glu), basic amino acids (Lys, Arg) as well as hydrophilic amino acids (e.g., Ser, Thr, Asn, Gln) and unnatural amino acids (e.g., dehydrobutyrine, dehydroalanine, phenylglycine, homophenylalanine, tetrahydro-isoquinoline-3-carboxylic acid (Tic), thienylalanine (Thi), 4-halophenylalanine, and etc.). The structural diversity achieved by the combination of these amino acids results in selectivity toward different histone deacetylases and reduced toxicity.

The present inventor created a variety of the modified FK228 analogues by changing the structure to achieve higher selectivity toward different histone deacetylases and assessed for their pharmacological profiles, such as potency, selectivity and their ability to induce HbF expression.

To evaluate anti-tumoral activity of the modified FK228 analogues, human transitional carcinoma cell lines T24, TCCSUP, 253J and human prostate cancer cell lines PC-3, LNCaP, Du-145 were cultured in T medium (Invitrogen) supplemented with 5% fetal bovine serum and 1% penicillin-streptomycin. $2 \times 10^3$ Cells in 50 μL of medium were plated into each well of a 96-well plate one day before adding compound. Each compound was diluted with DMSO to two folds of the concentrations, then 50 μL of the compound-containing medium was added into cells. Each treatment was in triplicate. Three days later, cell proliferation was measured with a cell proliferation kit (Roche). Briefly, 10 μL of MTT (3-[4,5-dimethylthiazol-2-yl]-2,5-diphenyl tetrazolium bromide) was added into each well for 4 hours, then 100 μL of the solubilization solution was added and cells were incubated for overnight. The spectrophotometrical absorbance of the samples was measured with a SpectraMax M5 plate reader (Molecular Devices) at 565 nm. The data were presented as percentage inhibition using non-treated cells as control.

Figure 9:
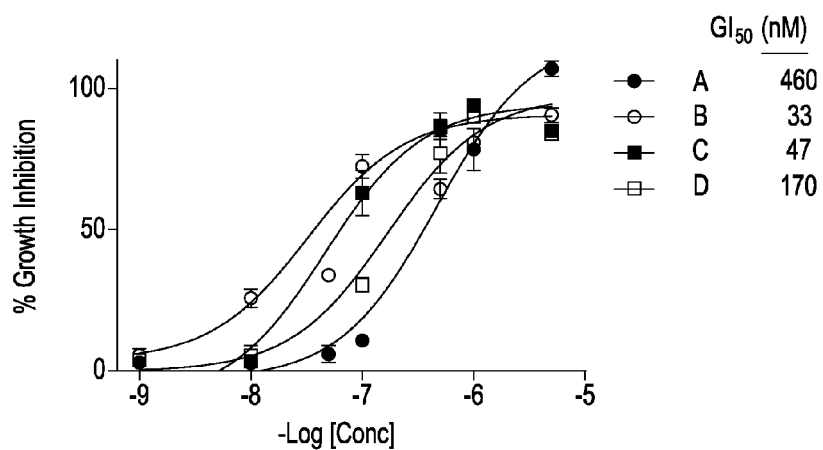
Figure 9:
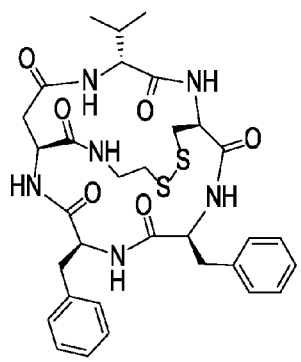
Figure 9:
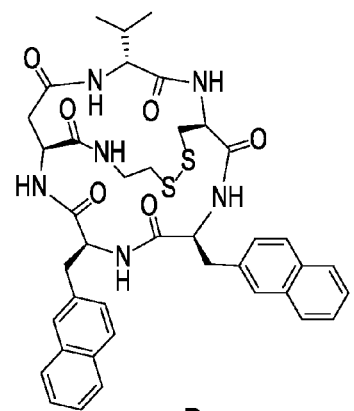
Figure 9:
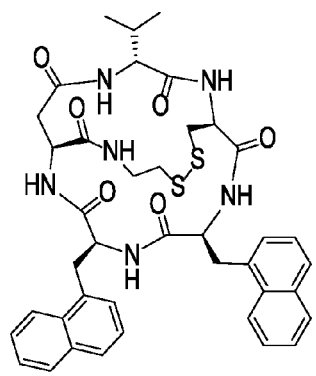
Figure 9:
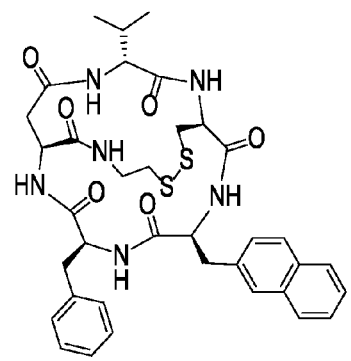

FIGS. 9-11 are graphs showing dose-dependent growth inhibition of cancer cells (prostate and bladder cancers) by modified FK228 analogues. Several compounds including A compound JMA26, B compound JMA33, C compound JMA46 and D compound JMA47 (FIG. 9) were found effective showing $GI_{50}$ values of 460 nM, 33 nM, 170 nM, and 47 nM, respectively. FIG. 10 includes the general structure in FIG. 10A including R groups. The R groups are defined in FIG. 10B and growth inhibition for the specific composition depicted in FIG. 10B are shown in FIG. 10C. The compound A compound JMA26 (same as compound 5h in FIG. 10) showed high cytotoxicity on a variety of cancer cells (3 prostate and 3 bladder cancer cells). Similarly, FIG. 11 includes the general structure in FIG. 1A including R groups. The R groups are defined in FIG. 1B and growth inhibition for the specific composition depicted in FIG. 10B are shown in FIG. 1C. FIG. 11 also demonstrates a range of anti-tumoral activity of modified FK228 analogues depending on their side chain functional groups. FIG. 11A is a structure of the modified FK228 analogues and the side chain functional groups of the structure in FIG. 11A is shown in FIG. 11B. FIG. 11C is a graph of the activity as a function of side chain seen in FIG. 11B.

The methods and compositions of the invention may be used to treat any cancer or cell proliferation, whether malignant or benign. In one important embodiment, the invention provides methods of treating particular types of malignant cancer. The skilled artisan will know of many different methods of administering the present invention to a subject depending on the location, type, stage of progression, age of subject, prior conditions, etc.

The term "delivering" or "administering" refers to making the composition of the present invention available to the interior or exterior of the tissue (e.g., tumor) to be treated such that the therapeutic agent is capable of having a therapeutic effect on the interior of the tissue and includes, for example, contacting the tissue with the agent. In addition, the present invention may be administered alone or in conjunction with other pharmacologically active agents, e.g., together with immunosuppressive agents, anticancer treatments, chemotherapy, antibiotics and/or antiviral agents. The present invention may be administered by: enteral, gastric feeding tube, duodenal feeding tube, gastrostomy, in suppository or enema form, parenteral, injection or infusion including intravenous, intraarterial, intramuscular, subcutaneous, intraosseous infusion, intradermal, intrathecal, intraperitoneal, transdermal, transmucosal, inhalational, epidural, intrathecal, intravitreal or other method known to the skilled artisan.

The present invention relates to methods for the preparation, use and as well as formulations containing modified FK228 analogues for the treatment and/or prevention of cancer. Although the modified FK228 analogues of the present invention are directed at treatments for cancer and other disease that are affected by histone deacetylase inhibitors and specifically FK228 histone deacetylase inhibitors, the subject may not have cancer, may be undergoing treatment for cancer, or may already have cancer, have cancer but no metastasis, have cancer and a metastatic cancer, have cancer that is in remission, have cancer that is immunosuppressed as a result of undergone anti-cancer therapy, chemotherapy, radiation or a combination thereof prior to administration of the invention.

The present invention may modulate the growth of one or more cells, e.g., a non-limiting list includes colon carcinoma cells, colorectal cancer cells, rectal carcinoma cells, hairy cell leukemia cells, osophogeal carcinoma cells, sarcoma cells, seminoma cells, angiosarcoma cells, carcinoma cells, chordoma cells, fibrosarcoma cells, myxosarcoma cells, liposarcoma cells, chondrosarcoma cells, osteogenic sarcoma cells, endotheliosarcoma cells, lymphangiosarcoma cells, lymphangioendotheliosarcoma cells, synovioma cells, mesothelioma cells, leiomyosarcoma cells, rhabdomyosarcoma cells, pancreatic cancer cells, breast cancer cells, ovarian cancer cells, prostate cancer cells, squamous cell carcinoma cells, basal cell carcinoma cells, adenocarcinoma cells, sweat gland carcinoma cells, sebaceous gland carcinoma cells, papillary carcinoma cells, papillary adenocarcinomas cells, cystadenocarcinoma cells, medullary carcinoma cells, bronchogenic carcinoma cells, renal cell carcinoma cells, hepatoma cells, bile duct carcinoma cells, choriocarcinoma cells, embryonal carcinoma cells, cervical cancer cells, testicular tumor cells, lung carcinoma cells, small cell lung carcinoma cells, bladder carcinoma cells, epithelial hemangioblastoma cells, acoustic neuroma cells, oligodendroglioma cells, meningioma cells, melanoma cells, neuroblastoma cells, retinoblastoma cells, acute lymphocytic leukemia cells, acute myelocytic leukemia cells, promyelocytic leukemia cells, myelomonocytic leukemia cells, monocytic leukemia cells, erythroleukemia leukemia cells, chronic myelocytic leukemia cells, chronic lymphocytic leukemia cells, polycythemia vera cells, lymphoma cells, hodgkin's disease cells, non-hodgkin's disease cells, multiple myeloma cells, waldenstrom's macroglobulinemia cells, ewing's tumor cells, wilms' tumor cells and combinations thereof.

The present invention may be administered orally in a sustained or immediate release form of a solution, an emulsion, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

The present invention provides modified FK228 compounds and a method of treating diseases related to the activity of a histone deacetylase in a subject by administering to the subject an effective amount of a modified FK228 compound includes an amino acid conjugate which constitutes an amino thiol, a hydroxy thiol, a dithiol, or a hydroxamic acid, instead of a hydroxy-mercapto-heptenoic acid moiety in FK228.

The amino acid includes L-aspartic acid, L-glutamic acid, L-homoglutamic acid, D-aspartic acid, D-glutamic acid, D-homoglutamic acid and the amino thiol includes a cysteamine. The modified FK228 compound may include one or more substitutions at any or all of the points about the modified FK228 compound and an amino acid conjugate which constitutes an amino thiol, a hydroxy thiol, a dithiol, or a hydroxamic acid. The substitutions may include a H, a C, a B, a N, a O, a S, a P, a Se, an lower alkyl, an alkoxy, an alkoxyalkyl, a hydroxy, a hydroxyalkyl, an alkenyl, an amino, an imino, a nitrate, an alkylamino, a dialkylamino, a nitro, a nitroso, an aryl, a biaryl, a polycyclic aromatic, an alkylaryl, an arylalkyl, an arylalkoxy, an arylalkylamino, a cycloalkyl, a bridged cycloalkyl, a cycloalkoxy, a cycloalkyl-alkyl, an arylthio, an alkylthio, an alkylsulfinyl, an alkylsulfonyl, an arylsulfonyl, an arylsulfinyl, a caboxamido, a carbamoyl, a hydroxamate, a carboxyl, a carbonyl, an alkoxycarbonyl, a halogen, a haloalkyl, a haloalkoxy, a heteroayl, a heterocyclic ring, an arylheterocyclic ring, a heterocyclic compound, an amido, an imido, a guanidino, a hydrazido, an aminoxy, an alkoxyamino, an urea, an alkylamido, a carboxylic ester, a thioether, a carboxylic acid, a phosphoryl group, a polycyclic aromatic and combinations thereof.

The present invention also provides a pharmaceutical composition and method for treating a subject that would medically benefit from either stimulation or inhibition of one or more histone deacetylases by administering to the subject a pharmaceutically effective amount of a modified FK228 compound having an amino acid conjugate which constitutes an amino thiol, a hydroxy thiol, a dithiol, or a hydroxamic acid, instead of a hydroxy-mercapto-heptenoic acid moiety in FK228. The modified FK228 compound functions to stimulate or inhibit the activity of one or more histone deacetylases.

The modified FK228 compound may be adapted for oral, dermatological, transdermal or parenteral administration and be in the form of a solution, an emulsion, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder. The modified FK228 compound may further include one or more of diluents excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof.

The amino acid includes L-aspartic acid, L-glutamic acid, L-homoglutamic acid, D-aspartic acid, D-glutamic acid, D-homoglutamic acid and the amino thiol includes a cysteamine. In addition, the modified FK228 compound, the amino acid and/or the amino thiol conjugate may include one or more substitutions selected from a H, a C, a N, a B, a O , a S, a P, a Se, an lower alkyl, an alkoxy, an alkoxyalkyl, a hydroxy, a hydroxyalkyl, an alkenyl, an amino, an imino, a nitrate, an alkylamino, a dialkylamino, a nitro, a nitroso, an aryl, a biaryl, a polycyclic aromatic, an alkylaryl, an arylalkyl, an arylalkoxy, an arylalkylamino, a cycloalkyl, a bridged cycloalkyl, a cycloalkoxy, a cycloalkyl-alkyl, an arylthio, an alkylthio, an alkylsulfinyl, an alkylsulfonyl, an arylsulfonyl, an arylsulfinyl, a caboxamido, a carbamoyl, a hydroxamate, a carboxyl, a carbonyl, an alkoxycarbonyl, a halogen, a haloalkyl, a haloalkoxy, a heteroaryl, a heterocyclic ring, an arylheterocyclic ring, a heterocyclic compound, an amido, an imido, a guanidino, a hydrazido, an aminoxy, an alkoxyamino, an urea, an alkylamido, a carboxylic ester, a thioether, a carboxylic acid, a phosphoryl group, a polycyclic aromatic and combinations thereof.

The present invention includes a compound having the formulas:

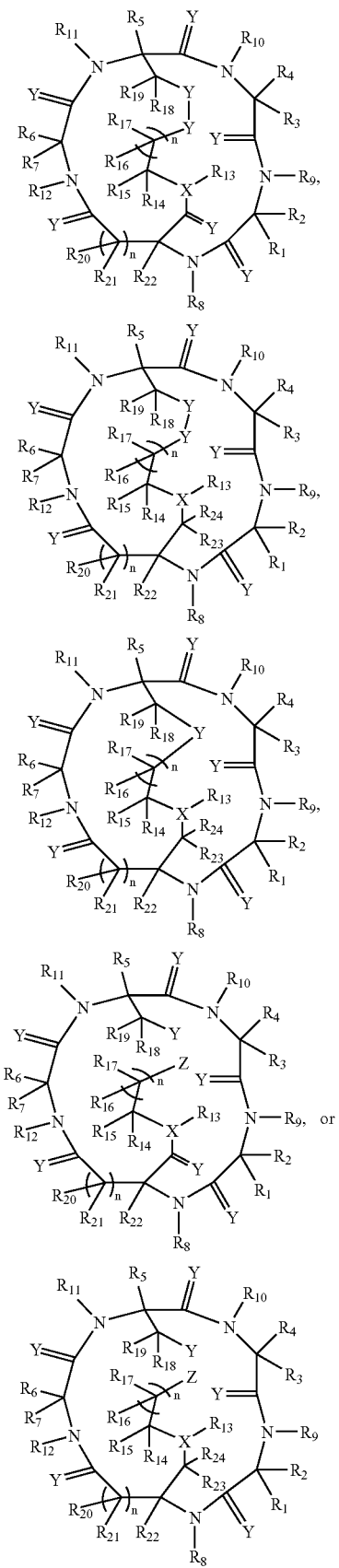

wherein X and Y includes independently a B, a C, a N, a O, a S, a P, or a Se, and R1-R24 and Z include independently one or more optionally substituted groups selected from a H, a B, a C, a N, a O, a S, a P, a Se, an lower alkyl, an alkoxy, an alkoxyalkyl, a hydroxy, a hydroxyalkyl, an alkenyl, an amino, an imino, a nitrate, an alkylamino, a dialkylamino, a nitro, a nitroso, an aryl, a biaryl, a polycyclic aromatic, an alkylaryl, an arylalkyl, an arylalkoxy, an arylalkylamino, a cycloalkyl, a bridged cycloalkyl, a cycloalkoxy, a cycloalkyl-alkyl, an arylthio, an alkylthio, an alkylsulfinyl, an alkylsulfonyl, an arylsulfonyl, an arylsulfinyl, a caboxamido, a carbamoyl, a hydroxamate, a carboxyl, a carbonyl, an alkoxycarbonyl, a halogen, a haloalkyl, a haloalkoxy, a heteroayl, a heterocyclic ring, an arylheterocyclic ring, a heterocyclic compound, an amido, an imido, a guanidino, a hydrazido, an aminoxy, an alkoxyamino, an urea, an alkylamido, a carboxylic ester, a thioether, a carboxylic acid, a phosphoryl group, a polycyclic aromatic and combinations thereof. And, n is 0, 1, 2, 3, 4, 5, 6, 7, etc.

The optionally substituted groups include a substitution selected from a BRR' (R and R' may be OH, H, OR, NR'R", halogen, alkyl groups), OH, OR, $NH_2$, NRR', NHOH, SH, SR, SeH, SeR, PRR', PORR', F, Cl, Br, I. In addition, an alkenyl group may be added at one or more locations selected from R1 and R2, R3 and R4, R6 and R7, R14 and R15, R16 and R17, R18 and R19, R20 and R21, and R23 and R24. For instance,

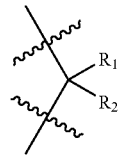

may be

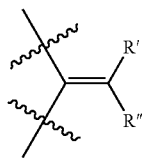

where R' and R" may be hydrogen, boron, optionally substituted lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkyl-alkyl, arylthio, alkylthio, alkylsulfinyl, alkylsulfonyl, arylsulfonyl, arylsulfinyl, caboxamido, carbamoyl, hydroxamate (C(O)NHOH), carboxyl, carbonyl, alkoxycarbonyl, halogen, haloalkyl, haloalkoxy, heteroayl, heterocyclic ring, arylheterocyclic ring, heterocyclic compound, amido, imido, guanidino, a hydrazido, an aminoxy, an alkoxyamino, an urea, alkylamido, carboxylic ester, thioether, carboxylic acid, phosphoryl group, polycyclic aromatic substituted with a BRR', OH, OR, $NH_2$, SH, SR, SeH, SeR, PRR', PORR', F, Cl, Br, I, NHR, NRR', $CN_3H_4$, a N, a O, a S, a P, a Se, a H, or combination thereof.

Alternatively, R' and R" may be one or more of the following:

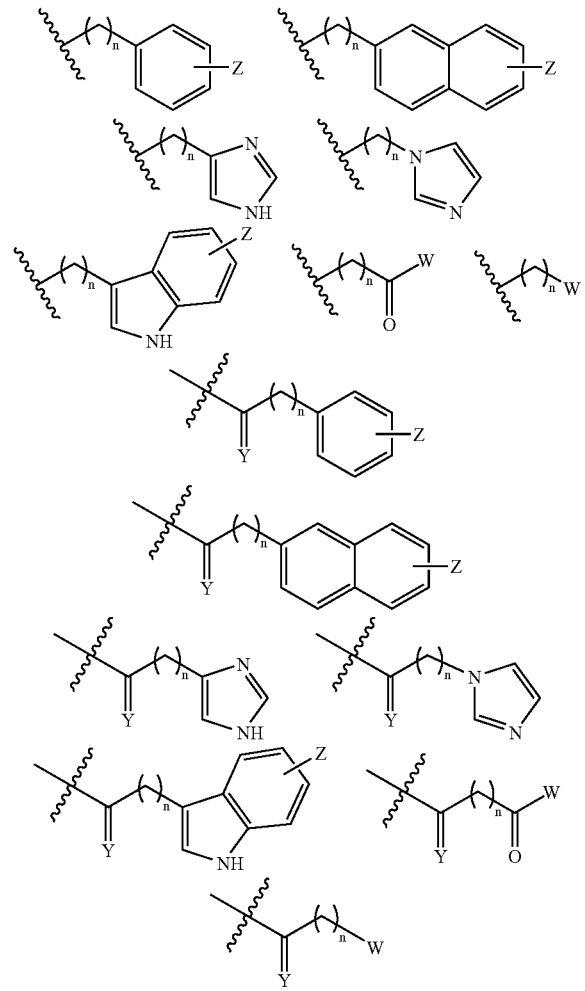

where Z is a BRR' (R and R' may be OH, H, OR, NR'R", halogen, alkyl groups), OH, OR, $NH_2$, NRR', NHOH, SH, SR, SeH, SeR, PRR', PORR', F, Cl, Br, I. W is a BRR' (R and R' may be OH, H, OR, NR'R", halogen, alkyl groups), an OH, an OR, a $NH_2$, a NHR, a NRR'(R, R' are alkyl groups), NHOH, and an imine (C(NH)R1R2. For example, when R1 is a $NH_2$ and $R_2$ is a NH the imine is actually a guanidine group), SH, SR, SeH, SeR, PRR', PORR', and n is 0, 1, 2, 3, 4, 5, 6, 7 etc. X and Y may be B, C, N, O, S, P, and Se.

The present invention provides modified FK228 compounds and a method of inducing γ-globin expression and HbF expression by administering to the subject an effective amount of a modified FK228 compound includes an amino acid conjugate which constitutes an amino thiol, a hydroxy thiol, a dithiol, or a hydroxamic acid, instead of a hydroxymercapto-heptenoic acid moiety in FK228.

Drug-mediated HbF induction remains the best approach to ameliorate the symptoms and complications of various conditions including SCD. The present invention uses molecular modeling to design novel HDAC inhibitors, which can be easily prepared with high efficiency. The present invention provides diverse structural analogues of the modified FK228 analogues that are synthesized using solid-phase synthesis technique. The present invention provides modified FK228 analogues that induce γ-globin expression. In addition the present invention provides modified FK228 analogues that inhibitors histone deacetylase while being a potent HbF inducer to affect the regulation one or more γ-globin gene to treatment sickle cell disease.

Generally, mutations in the gene coding sequences of the human globin genes lead to the class of disorders known as the hemoglobinopathies; over 1300 mutations have been discovered to date.[1] In humans, hemoglobin is encoded by genes in the α-locus on chromosome 16 and the β-globin locus located on chromosome 11. The latter consists of the ε, $^G\gamma\,^A\gamma$, δ and β globin genes expressed sequentially from 5' to 3' in a tissue- and developmental-specific manner.[2] The expression of genes in the β-locus is controlled by the locus control region positioned upstream of ε-globin, composed of five DNaseI hypersensitive sites,[3-5] each containing one or more binding motif for two hematopoietic-restricted proteins, GATA-1 and NF-E2[6-8] and other ubiquitous DNA-binding proteins. In particular, FOG (Friend of GATA) is co-expressed and interacts with GATA-1 to promote erythroid and megakaryocytic differentiation.[9] Two major switches occur in globin gene expression in the β-locus[10] from ε- to γ-globin around 6 weeks and from γ- to β-globin after birth. During fetal-stage development HbF ($α_2,γ_2$) is synthesized at high levels while adults hemoglobin A (HbA; $α_2,β_2$) is synthesized starting around 12 weeks of gestation and reaches high levels after birth and remains so throughout life.[2]

One of the most commonly encountered γ-globin hemoglobinopathy is sickle cell anemia caused by an A→T mutation at $β^6$ (GAG→GTG; Glu→Val)[11,12] to produce hemoglobin S (HbS) polypeptide chains. Sickle cell disease includes a heterogeneous group of disorders in which either two copies of the $β^S$ allele are present on chromosome 11 or one $β^S$ allele along with a second abnormal hemoglobin allele. The pathophysiology of SCD is based on HbS polymerization leading to the characteristic sickled red blood cells.[13] The hallmark symptoms are chronic hemolysis, anemia, pain and other complications related to vascular (vaso)-occlusion. However, the clinical phenotypes vary in part due to variable HbF levels.[14] Naturally occurring mutations in the γ-globin promoter produce hereditary persistence of HbF (HPFH) and ameliorate the symptoms of Sickle cell disease. Single nucleotide polymorphisms in the γ-gene promoters (non-deletion HPFH) or large deletions in the β-locus (deletional HPFH) can produce HPFH.[2] The present invention includes a method and composition for the regulation of γ-globin.

To date drug-mediated HbF induction has been the most effective approach to specific therapy for SCD short of bone marrow transplantation. Research efforts to understand mechanisms of hemoglobin switching and pharmacological agents capable of inducing HbF synthesis has shaped treatment progress over the last two decades.

At birth HbF comprises 80-90% of the total hemoglobin and it gradually decreases to <1% by 10 months in normal infants.[15] HbF is a heterogeneous mixture γ-globin polypeptide chains containing either glycine ($^Gγ$) or alanine ($^Aγ$) at residue 136.[16] At birth a switch to HbF consisting of $^Aγ$-chains arise. As the HbF level declines, it becomes restricted to a subset of erythrocytes called F-cells which is genetically controlled however the genes involved in this process are poorly understood.[17] The clinical efficacy of HbF in Sickle cell disease is due to its ability to dilute HbS below the threshold required for polymerization and formation of asymmetric hybrid HbF/S molecules.[18-20] Each γ-globin gene contains a canonical TATA box, duplicated CCAAT boxes and a single CACCC box.[2] A large number of proteins are capable of binding the proximal 200-bp region of the homologous γ-globin promoters.[2] The role of regulatory sites such as the stage selector element at −34[21] bound by CP2[22] and NF-E4,[23] the γ-globin CCAAT boxes[24-26] or the CACCC region where fetal Kiruppel-like factor (FKLF) and FKLF-2 bind[27,28] in the γ-globin promoter, remains to be determined in vivo. Moreover the role of repressor complexes such as DRED (direct repeat erythroid-definitive) located near the distal CAAT box[29] in HDAC-mediated chromatin remodeling to silence γ-globin expression remains to be determined as well.

Pharmacological fetal hemoglobin induction. Different classes of pharmacological agents that reactivate γ-globin expression have been identified. They include cytotoxic agents, DNA methyl transferases and histone deacetylase inhibitors. Cytotoxic compounds terminate actively cycling progenitors and perturb cellular growth to trigger rapid erythroid-regeneration and F-cell accumulation. S-stage-specific cytotoxic drugs such as cytosine arabinoside,[30] myleran,[31] vinblastine,[32] and hydroxyurea (HU)[33,34] induce HbF production in primates and humans.[33] The Multicenter Study of Hydroxyurea established the first drug treatment for SCD.[35] Hydroxyurea was shown to reduce vaso-occlusive episodes in the majority of patients treated. Limitations to using this agent such as bone marrow suppression[35] concerns over long term carcinogenic complications and a 30% non-response rat[36] make the development of alternative therapies desirable.

Figure 12A:
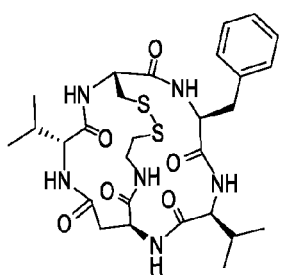
FIGS. 12A-12NNN are a series of non limiting examples of chemical compounds provided by the present invention.
Figure 12B:
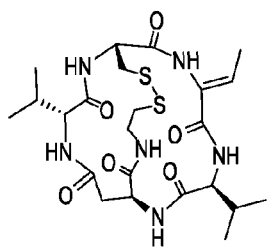
Figure 12C:
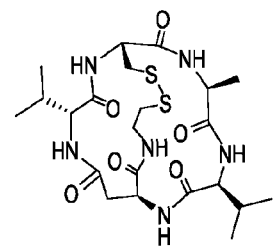
Figure 12D:
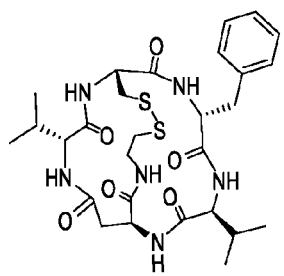
Figure 12E:
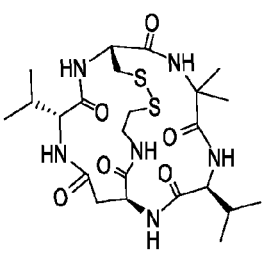
Figure 12F:
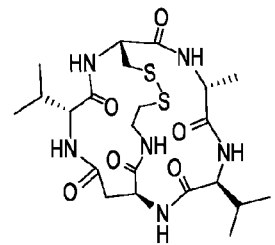
Figure 12:
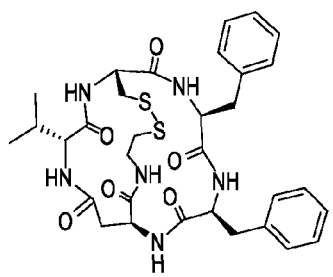
Figure 12:
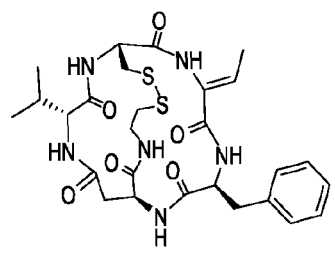
Figure 12:
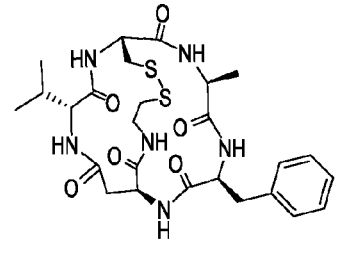
Figure 12G:
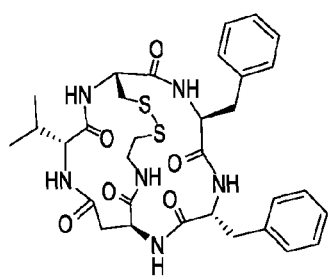
Figure 12H:
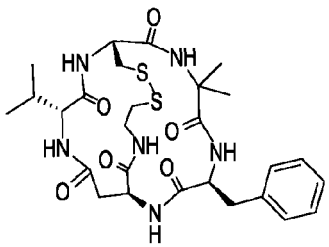
Figure 12I:
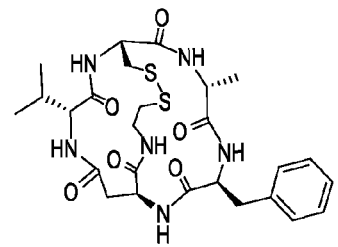
Figure 12J:
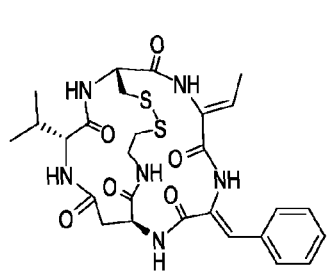
Figure 12K:
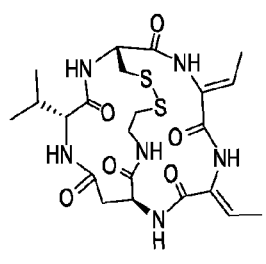
Figure 12L:
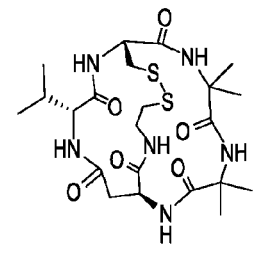
Figure 12M:
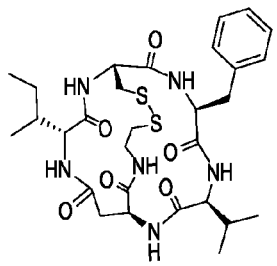
Figure 12N:
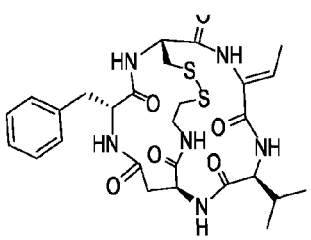
Figure 12O:
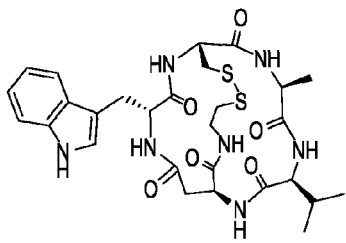
Figure 12P:
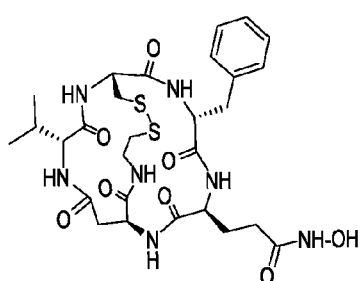
Figure 12Q:
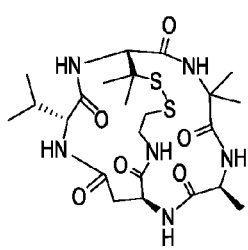
Figure 12R:
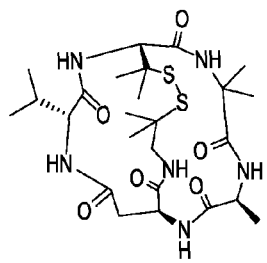
Figure 12S:
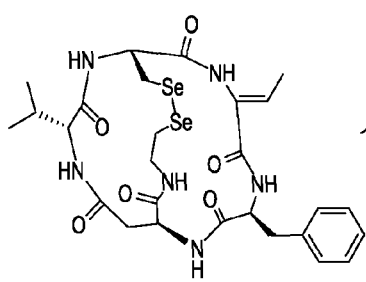
Figure 12T:
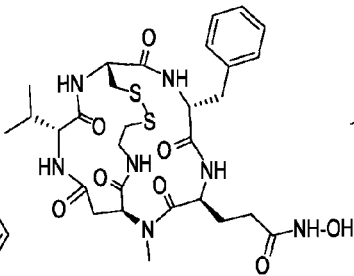
Figure 12U:
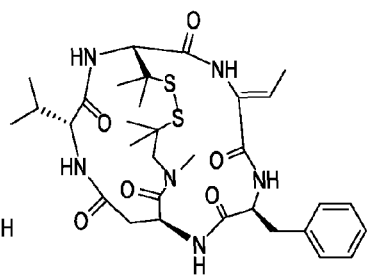
Figure 12V:
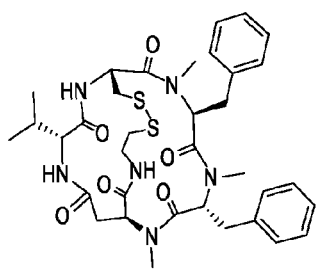
Figure 12W:
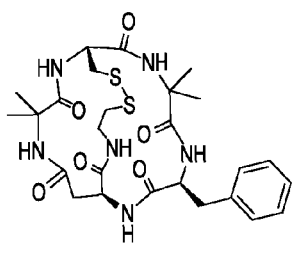
Figure 12X:
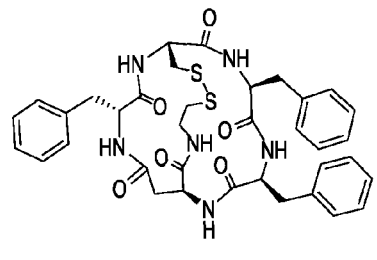
Figure 12Y:
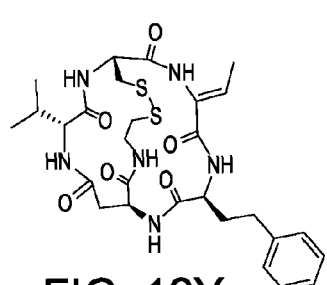
Figure 12Z:
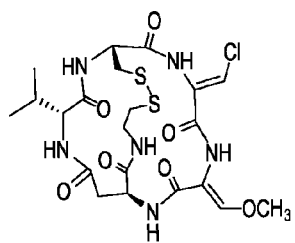
Figure 12A:
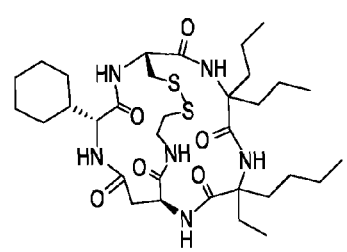

For example, a non-limiting list of sample chemical compounds provided by the present invention is provided in FIG. 12A-12NNN.

Figure 13:
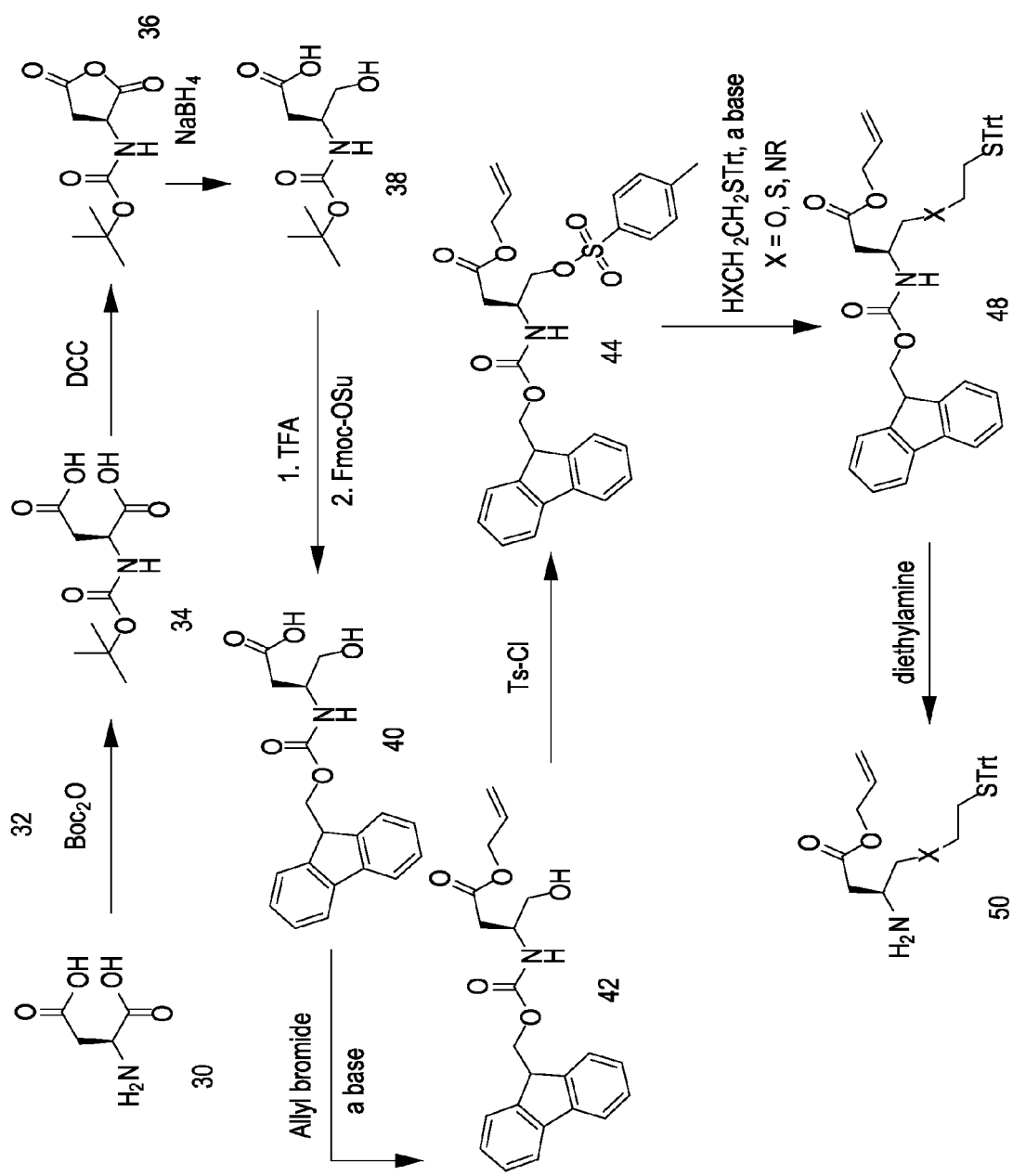
FIG. 13 is a schematic of one of the synthetic routes to make an amino acid conjugate which constitutes an amino thiol, a hydroxy thiol, or a dithiol instead of a hydroxy-mercapto-heptenoic acid moiety in FK228.

FIG. 13 is a schematic of one of the synthetic routes to make an amino acid conjugate, which constitutes an amino thiol, a hydroxy thiol, a dithiol, or a hydroxamic acid. To construct a FK228 analogue having an amino acid conjugate which constitutes an amino thiol, a hydroxy thiol, a dithiol, or a hydroxamic acid instead of a hydroxy-mercapto-heptenoic acid moiety in FK228, the amino acid conjugates were first synthesized. An amino group of an Asp 30 was protected with a Boc group 32, and the resulting Boc-Asp 34 was treated with DCC to give the anhydride 36 which was subsequently treated with sodium borohydride to produce the hydroxy acid 38. Then, the Boc group was changed to a Fmoc group and an allyl ester 42 was formed by the treatment of allyl bromide and a base. The hydroxy ester 42 was reacted with tosyl chloride and a base, and the resulting tosylate 44 was subsequently treated with a S-Trt-protected amino thiol, hydroxy thiol, or dithiol to form compound 48. Then, the removal of the Fmoc group by a base like piperidine or diethylamine yielded an amino acid conjugate 50 which constitutes an amino thiol, a hydroxy thiol, or a dithiol.

Figure 14:
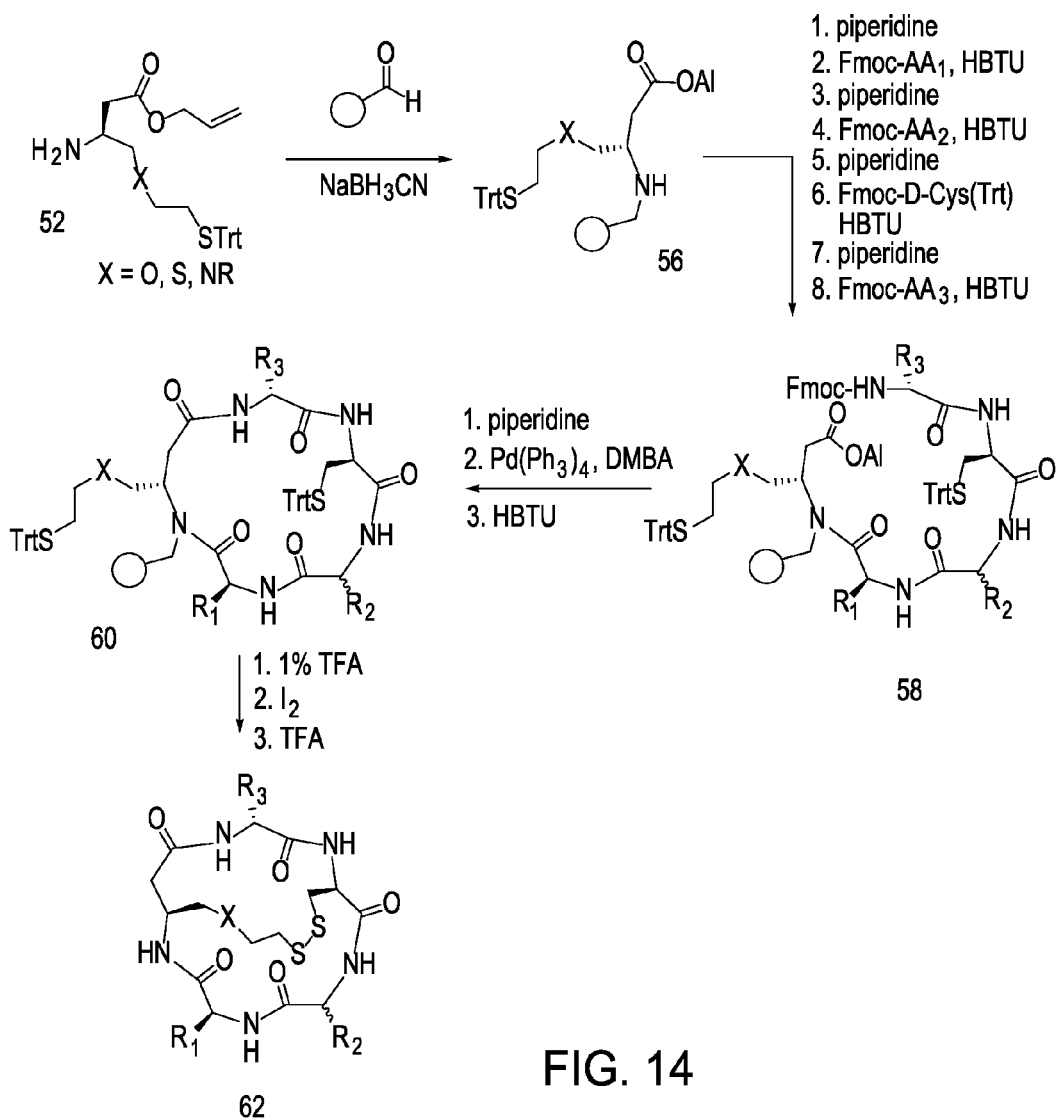
FIG. 14 is a schematic of one of the synthetic routes to make an FK228 analogue comprising of an amino acid conjugate which constitutes an amino thiol, a hydroxy thiol, or a dithiol instead of a hydroxy-mercapto-heptenoic acid moiety in FK228.

FIG. 14 is a schematic of one of the synthetic routes to make a FK228 analogue including an amino acid conjugate which constitutes an amino thiol, a hydroxy thiol, or a dithiol instead of a hydroxy-mercapto-heptenoic acid moiety in FK228. An amino acid conjugate 52 which constitutes an amino thiol, a hydroxy thiol, or a dithiol was anchored to polystyrene resin 54 using a backbone amide linker and sodium cyanoborohydride to produce the compound 56. To the compound 56, four Fmoc-amino acids were consecutively coupled to give a linear pentapeptide 58. The Fmoc and allyl groups were selectively removed and a macrolactam 60 was formed by the treatment of a coupling reagent like HBTU or BOP. After the removal of Trt protecting groups with a dilute TFA solution, a disulfide bond was created by the treatment of iodine. Then, a FK228 analogue 62 comprising of an amino acid conjugate which constitutes an amino thiol, a hydroxy thiol, or a dithiol instead of a hydroxy-mercapto-heptenoic acid moiety in FK228 was released from the resin by TFA.

Figure 15:
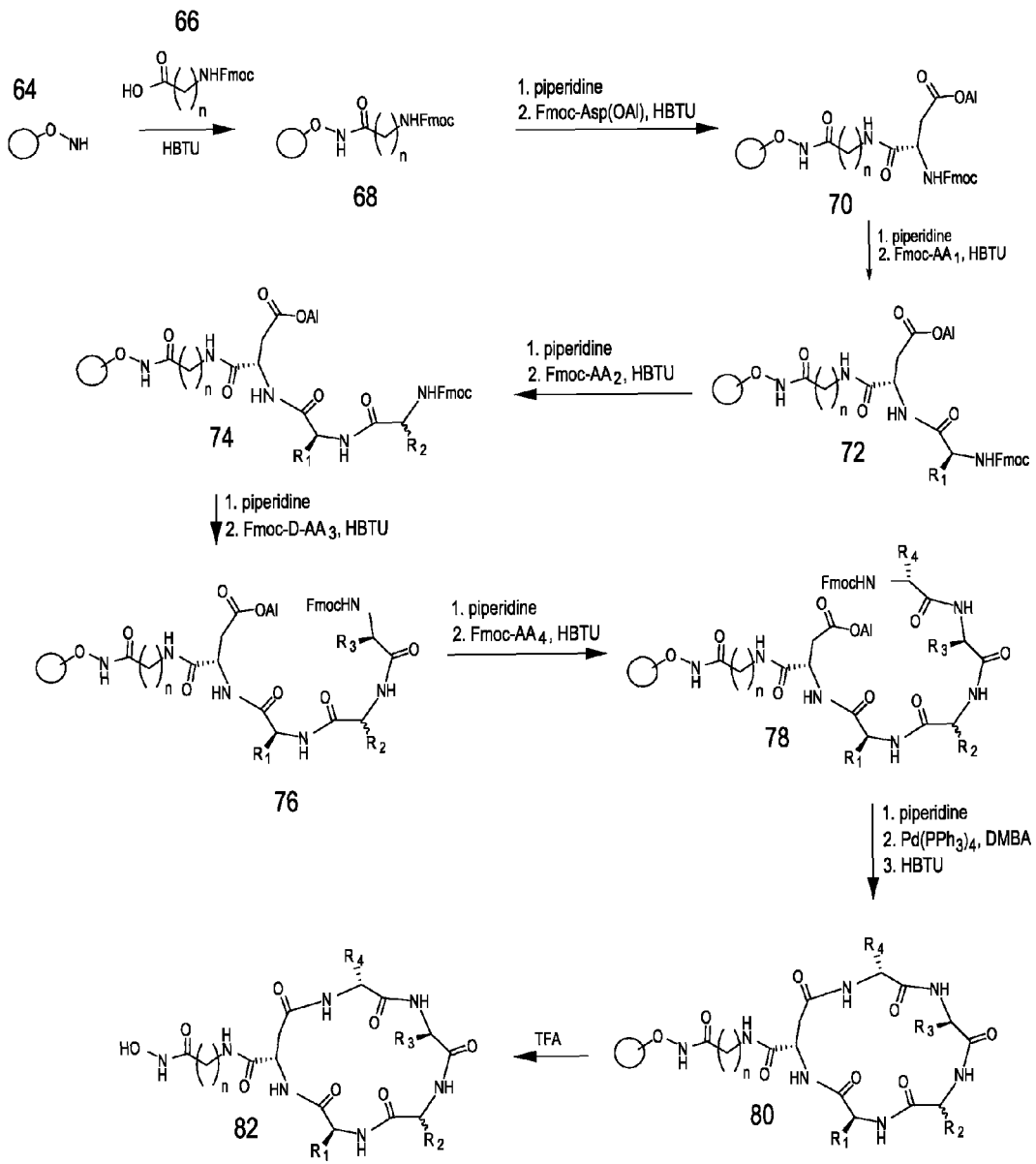
FIG. 15 is a schematic of one of the synthetic routes to make an FK228 analogue comprising of an amino acid conjugate which constitutes a hydroxamic acid instead of a hydroxy-mercapto-heptenoic acid moiety in FK228.

FIG. 15 is a schematic of one of the synthetic routes to make an FK228 analogue comprising of an amino acid conjugate which constitutes a hydroxamic acid instead of a hydroxy-mercapto-heptenoic acid moiety in FK228. Hydroxylamino-polystyrene resin 64 was reacted with a Fmoc-protected ω-amino acid 66 like a glycine, a beta-alanine, a 4-aminobutanoic acid, a 5-aminopentanoic acid, or a 6-aminohexanoic acid and a coupling reagent like HBTU or BOP. The Fmoc group of the resulting ω-amino acid anchored to the resin 68 was removed by a base like piperidine or diethylamine and subsequent coupling of Fmoc-Asp(OAl) produced the dipeptide 70. To the dipeptide 70, four Fmoc-amino acids were consecutively coupled using standard Fmoc/tBu solid-phase peptide synthesis protocol to produce peptide 74, 76, and 78. The allyl and Fmoc groups of the linear hexapeptide 78 were removed and a macrolactam 80 was formed by treating a coupling reagent like HBTU or BOP. A FK228 analogue containing a hydroxamic acid moiety 82 was released from the resin by TFA.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Hardison, R., Riemer, C., Chui, D. H., Huisman, T. H., and Miller, W. Electronic access to sequence alignments, experimental results, and human mutations as an aid to studying globin gene regulation. (1998) Genomics 47, 429-437.
2. Stamatoyannopoulous, G., and Grosveld, F. (2001) Hemoglobin switching. In: Stamatoyannopoulos, G., Majerus, P. W., Perlmutter, R. M., and Varmus, H. (eds). The Molecular Basis of Blood Disease, 3 Ed., Saunders, Philadelphia.
3. Kollias, G., Wrighton, N., Hurst, J., and Grosveld, F. Regulated expression of human Aγ-, β-, and hybrid βγ-globin genes in transgenic mice: manipulation of the developmental expression patterns. (1986) Cell 46, 89-94.
4. Grosveld, F., van Assendelft, G. B., Greaves, D. R., and Kollias, G. Position independent, high-level expression of the human β-globin gene in transgenic mice. (1987) Cell 51, 975-985.
5. Forrester, W. C., Takegawa, S., Papayannopoulou, T., Stamatoyannopoulos, G., and Groudine, M. Evidence for a locus activation region: the formation of developmentally stable hypersensitive sites in globin expressing hybrids. (1987) Nucleic Acids Res. 15, 10159-10177.
6. Martin, D. I., and Orkin, S. H. Transcriptional activation and DNA binding by the erythroid factor GF-1/NF-E1/Eryf 1. (1990) Genes Dev. 4, 1886-1898.
7. Goodwin, A. J., McInerney, J. M., Glander, M. A., Pomerantz, O., and Lowrey, C. H. In vivo formation of a human beta-globin locus control region core element requires binding sites for multiple factors including GATA-1, NF-E2, erythroid Kruppel-like factor, and Sp1. (2001) J. Biol. Chem. 276, 26883-26892.
8. Ney, P. A., Sorrentino, B. P., Lowrey, C. H., and Nienhuis, A. W. Inducibility of the HS II enhancer depends on binding of an erythroid specific nuclear protein. (1990) Nucleic Acids Res. 18, 6011-6017.
9. Wood, W. G., Bunch, C., Kelly, S., Gunn, Y., and Breckon, G. Control of haemoglobin switching by a developmental clock. (1985) Nature 313, 320-323.
10. Ingram, V. M. Gene mutations in human haemoglobin: the chemical difference between normal and sickle haemoglobin. (1957) Nature 180, 326-328.
11. Marotta, C. A., Forget, B. G., Cohen-Solal, M., and Weissman, S. M. Nucleotide sequence analysis of coding and noncoding regions of human beta-globin mRNA. (1976) Prog. Nucleic Acid Res. Mol. Biol. 19, 165-175.
12. Browne, P., Shalev, O., and Hebbel, R. P. The molecular pathobiology of cell membrane iron: the sickle red cell as a model. (1998) Free Radic. Biol. Med. 24, 1040-1048.
13. Platt, O, S., Thorington, B. D., Brambilla, D. J., Milner, P. F., Rosse, W. F., Vichinsky, E., and Kinney, T. R. Pain in sickle cell disease. Rates and risk factors. (1991) N. Engl. J. Med. 325, 11-16.
14. Maier-Redelsperger, M., Noguchi, D., Montalembert, M., Rodgers, G. P., Schechter, A. N., Gourbil, A., Blanchard, D., Jais, J. P., Ducrocq, R., and Peltier, J. Y. Variation in fetal hemoglobin parameters and predicted hemoglobin S polymerization in sickle cell children in the first two years of life: Parisian Prospective Study on Sickle Cell Disease. (1994) Blood 84, 3182-3188.
15. Schroeder, W. A., Huisman, T. H., Shelton, J. B., Kleihauer, E. F., Dozy, A. M., and Roberson, B. Evidence for multiple structural genes for the gamma chain of human fetal hemoglobin. (1968) Proc. Natl. Acad. Sci. U.S.A. 60, 537-544.
16. Wood, W. G. Increased HbF in adult life. (1993) Baillieres. Clin. Haematol. 6, 177-213.
17. Bookchin, R. M., Nagel, R. L., and Balaza, T. Role of hybrid tetramer formation in gelation of haemoglobin S. (1975) Nature 256, 667-668
18. Bookchin, R. M., Balaza, T., Nagel, R. L., and Tellez, I. Polymerisation of haemoglobin SA hybrid tetramers. (1977) Nature 269, 526-527.
19. Nagel, R. L., Bookchin, R. M., Johnson, J., Labie, D., Wajcman, H., Isaac-Sodeye, W. A., Honig, G. R., Schiliro, G., Crookston, J. H., and Matsutomo, K. Structural bases of the inhibitory effects of Hb F and A2 on the polymerization of Hb S. (1979) Proc. Natl. Acad. Sci. U.S.A. 76, 670-672.
20. Papayannopoulou, T., Torrealba de Ron, A., Veith, R., Knitter, G., and Stamatoyannopoulos, G. Arabinosylcytosine induces fetal hemoglobin in baboons by perturbing erythroid cell differentiation kinetics. (1984) Science 224, 617-619.
21. Liu, D. P., Liang, C. C., Ao, Z. H., Jia, P. C., Chen, S. S., Wang, R. X., Liu, L. J., Jin, H. Q., Zha, D. Y., and Huang, Y. W. Treatment of severe beta-thalassemia (patients) with myleran. (1990) Am. J. Hematol. 33, 50-55.
22. Veith, R., Papayannopoulou, T., Kurachi, S., and Stamatoyannopoulos, G. Treatment of baboon with vinblastine: insights into the mechanisms of pharmacologic stimulation of Hb F in the adult. (1985) Blood 66, 456-459.
23. Galanello, R., Stamatoyannopoulos, G., and Papayannopoulou, T. Mechanism of Hb F stimulation by S-stage compounds. In vitro studies with bone marrow cells exposed to 5-azacytidine, Ara-C, or hydroxyurea. (1988) J. Clin. Invest. 81, 1209-1216.
24. Letvin, N. L., Linch, D.C., Beardsley, G. P., McIntyre, K. W., and Nathan, D. G. Augmentation of fetal-hemoglobin production in anemic monkeys by hydroxyurea. (1984) N. Engl. J. Med. 310, 869-873.
25. Charache, S., Terrin, M. L., Moore, R. D., Dover, G. J., Barton, F. B., Eckert, S. V., McMahon, R. P., and Bonds, D. R. Effect of hydroxyurea on the frequency of painful crises in sickle cell anemia. Investigators of the Multicenter Study of Hydroxyurea in Sickle Cell Anemia. (1995)N. Engl. J. Med. 332, 1317-1322.
26. Steinberg, M. H., Lu, Z. H., Barton, F. B., Terrin, M. L., Charache, S., and Dover, G. J. Fetal hemoglobin in sickle cell anemia: determinants of response to hydroxyurea. Multicenter Study of Hydroxyurea. (1997) Blood 89, 1078-1088.

27. de la Cruz, X., Lois, S., Sanchez-Molina, S., and Martinez-Balbas, M. A. Do protein motifs read the histone code. (2005) Bioessays 27, 164-165.

28. Ahn, S. H., Cheung, W. L., Hsu, J. Y., Diat, R. L., Smith, M. M., and Allis, C. D. Sterile 20 kinase phosphorylates histone H2B at serine10 during hydrogen peroxide induced apoptosis in S. cerevisiae. (2005) Cell 120, 25-36.

29. Kornberg, R. D. Eukaryotic transcriptional control. (1999) Trends Cell. Biol. 9, M46-M49

30. Watson, R. E., and Goodman, J. L. Epigenetics and DNA methylation come of age in toxicology. (2002) Toxicol. Sci. 67, 11-16.

31. Hansen, J. C. Conformational dynamics of the chromatin fiber in solution: determinants, mechanisms, and functions. (2002) Annu. Rev. Biophys. Biomol. Struct. 31, 361-392.

32. Carruthers, L. M., and Hansen, J. C. The core histone N termini function independently of linker histones during chromatin condensation. (2000) J. Biol. Chem. 275, 37285-37290.

33. Gill, G. SUMO and ubiquitin in the nucleus: different functions, similar mechanisms. (2004) Genes Dev. 18, 2046-2059.

34. Cohen-Armon, M., Visochek, L., Katzoff, A., Levitan, D., Susswein, A. J., Klein, R., Valbrun, M., and Schwartz, J. H. Long-term memory requires ADP-ribosylation. (2004) Science 304, 1820-1822.

35. Verdone, L., Caserta, M., and Di Mauro, E. Role of histone acetylation in the control of gene expression. (2005) Biochem. Cell Biol. 83, 344-353.

36. Klose, R. J., and Bird, A. P. Genomic DNA methylation: the mark and its mediators. (2006) Trends Biochem. Sci. 31, 89-97

37. Shilatford et al. Maintenance of low histone ubiquitylation by Ubp10 correlates with telomere proximal Sir2 association and gene silencing. (2005) Mol. Cell. 17, 585-594.

38. Lee, K. K., Florens, L., Swanson, S. K., Washburn, M. P., and Workman, J. L. The deubuitylation of Ubp8 is dependent upon Sgfl 1 and association with the SAGA complex. (2005) Mol. Cell. Biol. 25, 1173-1182.

39. Ingvarsdottir, K., Krogan, N. J., Emre, N. C., Wyce, A., Thompson, N. J., Emili, A., Hughes, T. R., Greenblatt, J. F., and Berger, S. L. $H_2B$ ubiquitin protease Ubp8 and Sgf11 constitute a discrete functional module with the S. cerevisiae SAGA complex. (2005) Mol. Cell. Biol. 26, 1162-1172.

40. Hassig, C. A., and Schreiber, S. L. Nuclear histone acetylases and deacetylases and transcriptional regulation: HATs off to HDACs. (1997) Curr. Opin. Chem. Biol. 1, 300-308.

41. Gregoretti, I. V., Lee, Y. M., and Goodson, H. V. Molecular evolution of the histone deacetylase family: functional implications of phylogenetic analysis. (2000) J. Mol. Biol. 338, 17-31.

42. Berger, S. L. Histone modifications in transcriptional regulation. (2002) Curr. Opin. Genet. Dev. 12, 142-148.

43. Zhang, Y., and Reinberg, D. Transcription regulation by histone methylation: Interplay between different covalent modifications of the core histone tails. (2001) Genes Dev. 15, 2343-2360.

44. Strahl, B. D., and Allis, C. D. The language of covalent histone modifications. (2000) Nature 403, 41-45.

45. Becker, P. B., and Horz, W. ATP-dependent nucleosome remodeling. (2002) Annu. Rev. Biochem. 71, 247-273.

46. Lusser, A., and Kadonaga, J. T. Chromatin remodeling by ATP-dependent molecular machines. (2003) Bioessays 25, 1192-1200.

47. Johnson, J., Hunter, R., McElveen, R., Qian, X. H., Baliga, B. S., and Pace, B. S. Fetal hemoglobin induction by the histone deacetylase inhibitor, scriptaid. (2005) Cell. Mol. Biol. 51, 229-238.

48. Turner, B. M. Histone acetylation and control of gene expression. (1991) J. Cell. Sci. 99, 13-20.

49. Mizzen, C. A., and Allis, C. D. Linking histone acetylation to transcriptional regulation. (1998) Cell. Mol. Life. Sci. 54, 6-20.

50. Kuo, M. H., and Allis, C. D. Roles of histone acetyltransferases and deacetylases in gene regulation. (1998) Bioessays 20, 615-626.

51. Johnstone, R. W. Histone-deacetylase inhibitors: novel drugs for the treatment of cancer. (2002) Nat. Rev. Drug Discov. 1, 287-299.

52. Marks, P. A., and Jiang, X. Histone deacetylase inhibitors in programmed cell death and cancer therapy. (2005) Cell Cycle 4, 549-551.

53. Monneret, C. Histone deacetylase inhibitors. (2005) Eur. J. Med. Chem. 40, 1-13.

54. Prasad, K. N. Butyric acid: a small fatty acid with diverse biological functions. (1980) Life Sci. 27, 1351-1358.

55. Gore, S. D., and Carducci, M. A. Modifying histones to tame cancer: clinical development of sodium phenylbutyrate and other histone deacetylase inhibitors. (2000) Exp. Opin. Invest. Drugs 9, 2923-2934.

56. Yamashita, T., Wakao, H., Miyajuma, A., and Asano, S. Differentiation inducers modulate cytokine signaling pathways in a murine erythroleukemia cell line. (1998) Cancer Res. 58, 556.

57. Witt, O., Sand, K., and Pekrun, A. Butyrate-induced erythroid differentiation of human K562 leukemia cells involves inhibition of ERK and activation of p38 MAP kinase pathways. (2000) Blood 95, 2391-2396.

58. Pace, B. S., Qian, X. H., Sangerman, J., Ofori-Acquah, S. F., Baliga, B. S., Han, J., and Critz, S. D. p38 MAP kinase activation mediates gamma-globin gene induction in erythroid progenitors. (2003) Exp. Hematol. 31, 1089-1096.

59. Torkelson, S., White, B., Faller, D. V., Phipps, K., Pantazis, C., and Perrine, S. P. Erythroid progenitor proliferation is stimulated by phenoxyacetic and phenylalkyl acids. (1996) Blood Cells Mol. Dis. 22, 150-158.

60. Dover, G. J., Brusilow, S., and Charache, S. Induction of fetal hemoglobin production in subjects with sickle cell anemia by oral sodium phenylbutyrate. (1994) Blood 84, 339-343.

61. Liakopoulou, E., Blau, C. A., Li, Q., Josephson, B., Wolf, J. A., Foumarakis, B., Raisys, V., Dover, G., Papayannopoulou, T., and Stamatoyannopoulos, G. Stimulation of fetal hemoglobin production by short chain fatty acids. (1995) Blood 86, 3227-3235.

62. Tsuji, N., Kobayashi, M., Nagashima, K., Wakisaka, Y., and Koizumi, K. A new antifungal antibiotics, trichostatin. (1976) J. Antibiot. 29, 1-6.

63. Yoshida, M., Kijima, M., Akita, M., and Beppu, T. Potent and specific inhibition of mammalian histone deacetylase both in vivo and in vitro by trichostatin A. (1990) J. Biol. Chem. 265, 17174-17179.

64. Finnin, M. S., Donigian, J. R., Cohen, A., Richon, V. M., Rifkind, R. A., Marks, P. A., Breslow, R., and Pavletch, N. P. Structures of a histone deacetylase homologue bound to the TSA and SAHA inhibitors. (1999) Nature 401, 188-193.

65. Richon, V. M., Emiliani, S., Verdin, E., Webb, Y., Breslow, R., Rifkind, R. A., and Marks, P. A. A class of hybrid polar inducers of transformed cell differentiation inhibits histone deacetylases. (1998) Proc. Natl. Acad. Sci. U.S.A. 95, 3003-3007.

66. Butler, L. M., Agus, D. B., Scher, H. I., Higgins, B., Rose, A., Cordon-Cardo, C., Thaler, H. T., Rifkind, R. A., Marks, P. A., and Richon, V. M. Suberoylanilide hydroxamic acid, an inhibitor of histone deacetylase, suppresses the growth of prostate cancer cells in vitro and in vivo. (2000) Cancer Res. 60, 5165-5170.

67. Marks, P. A., Richon, V. M., Breslow, R., and Rifkind, R. A. Histone deacetylase inhibitors as new cancer drugs. (2001) Curr. Opin. Oncol. 13, 477-483.

68. Itazaki, H., Nagashima, K., Sugita, K., Yoshida, H., Kawamura, Y., Yasuda, Y., Matsumoto, K., Ishii, K., Uotani, N., and Nakai, H. Isolation and structural elucidation of new cyclotetrapeptides, trapoxins A and B, having detransformation activities as antitumor agents. (1990) J. Antibiot. 43, 1524-1532.

69. Kijima, M., Yoshida, M., Suguta, K., Horinouchi, S., and Beppu, T. Trapoxin, an antitumor cyclic tetrapeptide, is an irreversible inhibitor of mammalian histone deacetylase. (1993) J. Biol. Chem. 268, 22429-22435.

70. Komatsu, Y., Tomizaki, K.-Y., Tsukamoto, M., Kato, T., Nishino, N., Sato, S., Yamori, T., Tsuruo, T., Furumai, R., Yoshida, M., Horinouchi, S., and Hayashi, H. Cyclic hydroxamic-acid-containing peptide 31, a potent synthetic histone deaceylase inhibitor with antitumor activity. (2001) Cancer Res. 61, 4459-4466.

71. Furumai, R., Komatsu, Y., Nishino, N., Khochbin, S., Yoshida, M., and Horinouchi, S. Potent histone deacetylase inhibitors built from trichostatin A and cyclic tetrapeptide antibiotics including trapoxin. (2001) Proc. Natl. Acad. Sci. U.S.A. 98, 87-92.

72. Jose, B., Okamura, S., Kato, T., Nishino, N., Sumida, Y., and Yoshida, M. Toward an HDAC6 inhibitor: synthesis and conformational analysis of cyclic hexapeptide hydroxamic acid designed from □-tubulin sequence. (2004) Bioorg. Med. Chem. 12, 1351-1356.

73. Nishino, N., Jose, B., Okamura, S., Ebisusaki, S., Kato, T., Sumida, Y., and Yoshida, M. Cyclic tetrapeptides bearing a sulfhydryl group potently inhibit histone deacetylases. (2003) Org. Lett. 5, 5079-5082.

74. Sandor, V., Senderowicz, A., Mertins, S., Sackett, D., Sausville, E., and Blagosklonny, M. V. P21-dependent Glarrest with downregulation of cyclin D1 and upregulation of cyclin E by the histone deacetylase inhibitor FR901228. (2000) Br. J. Cancer 83, 817-825.

75. Ruefli, A. A., Ausserlechner, M. J., Bernhard, D., Sutton, V. R., Tainton, K. M., and Kofler, R. The histone deacetylase inhibitor and chemotherapeutic agent suberoylanilide hydroxamic acid (SAHA) induces a cell-death pathway characterized by cleavage of Bid and production of reactive oxygen species. (2001) Proc. Natl. Acad. Sci. U.S.A. 98, 10833-10838.

76. Peart, M. J., Tainton, K. M., Ruefli, A. A., Dear, A. E., Sedelies, K. A., and O'Reilly, L. A. Novel mechanisms of apoptosis induced by histone deacetylase inhibitors. (2003) Cancer Res. 63, 4460-4471.

77. Peedicayil, J. Epigenetic therapy—a new development in pharmacology. (2006) Indian J. Med. Res. 123, 17-24.

78. Yamada, H., Arakawa, Y., Saito, S., Agawa, M., Kano, Y., and Horiguchi, Y. Depsipeptide-resistant KU812 cells show reversible P-glycoprotein expression, hyper-acetylated histones, and modulated gene expression profile. (2006) Leukemia Res. 30, 723-734.

79. Piekarz, R., and Bates, S. A review of depsipeptide and other histone deacetylase inhibitors in clinical trials. (2004) Curr. Pharm. Des. 10, 2289-2298.

80. Ueda, H., Nakajima, H., Hori, Y., Fujita, T., Nishimura, M., Goto, T., and Okuhara, M. FR901228, a novel antitumor bicyclic depsipeptide produced by *Chromobacterium violaceum* No. 968.1. Taxonomy, fermentation, isolation, physicochemical and biological properties, and antitumor activity. (1994) J. Antibiot. 47, 301-310.

81. Furumai, R., Matsuyama, A., Kobashi, N., Lee, K.-H., Nishiyama, M., Nakajima, H., Tanaka, A., Komatsu, Y., Nishino, N., Yoshida, M., and Horinouchi, S. FK228 (depsipeptide) as a natural prodrug that inhibits class I histone deacetylases. (2002) Cancer Res. 62, 4916-4921.

82. Xiao, J. J., Byrd, J., Marcucci, G., Grever, M., and Chan, K. K. Identification of thiols and glutathione conjugates of depsipeptide FK228 (FR901228), a novel histone protein deacetylase inhibitor, in the blood. (2003) Rapid Commun. Mass Spectrom. 17, 757-766.

83. Ueda, H., Nakajima, H., Hori, Y., Goto, T., and Okuhara, M. Action of FR901228, a novel antitumor bicyclic depsipeptide produced by *Chromobacterium violaceum* no. 968, on Ha-ras transformed NIH3T3 cells. (1994) Biosci. Biotechnol. Biochem. 58, 1579-1583.

84. Kosugi, H., Ito, M., Yamamoto, Y., Towatari, M., and Ueda, R. In vivo effects of a histone deacetylase inhibitor, FK228, on human acute promyelocytic leukemia in NOD/Shi-scid/scid mice. (2001) Jpn. J. Cancer Res., 529-536.

85. Fecteau, K. A., Mei, J., and Wang, H. C. Differential modulation of signaling pathways and apoptosis of ras-transformed 10T1/2 cells by the depsipeptide FR901228. (2002) J. Pharmacol. Exp. Ther. 300, 890-899.

86. Sutheesophon, K., Nishimura, N., Kobayashi, Y., Furukawa, Y., Kawano, M., Itoh, K., Kano, Y., Ishii, H., and Furukawa, Y. Involvement of the tumor necrosis factor (TNF)/TNF receptor system in leukemic cell apoptosis induced by histone deacetylase inhibitor depsipeptide (FK228). (2005) J. Cell. Physiol. 203, 387-397.

87. Cao, H., and Stamatoyannopoulos, G. Histone deacetylase inhibitor FK228 is a potent inducer of human fetal hemoglobin. (2006) Am. J. Hematol. 81, 981-983.

88. Ikuta, T., Kan, Y. W., Swerdlow, P. S., Faller, D. V., and Perrine, S. P. Alterations in protein-DNA interactions in the gamma-globin gene promoter in response to butyrate therapy. (1998) Blood 92, 2924-2933.

89. Perrine, S. P., Ginder, G. D., Faller, D. V., Dover, G. H., Ikuta, T., Witkowska, H. E., Cai, S. P., Vichinsky, E. P., and Olivieri, N. F. A short-term trial of butyrate to stimulate fetal-globin-gene expression in the beta-globin disorders. (1993) N. Engl. J. Med. 328, 81-86.

90. Atweh, G. F., Sutton, M., Nassif, I., Boosalis, V., Dover, G. J., Wallenstein, S., Wright, E., McMahon, L., Stamatoyannopoulos, G., Faller, D. V., and Perrine, S. P. Sustained induction of fetal hemoglobin by pulse butyrate therapy in sickle cell disease. (1999) Blood 93, 1790-1797.

91. Pace, B. S., Li, Q., and Stamatoyannopoulos, G. In vivo search for butyrate responsive sequences using transgenic mice carrying A gamma gene promoter mutants. (1996) Blood 88, 1079-1083.

92. Ikuta, T., Ausenda, S., and Cappellini, M. D. Mechanism for fetal globin gene expression: role of the soluble guanylate cyclase-cGMP-dependent protein kinase pathway. (2001) Proc. Natl. Acad. Sci. U.S.A. 98, 1847-1852.

93. Pace, B. S., Chen, Y. R., Thompson, A., and Goodman, S. R. Butyrate-inducible elements in the human gamma-globin promoter. (2000) Exp. Hematol. 28, 283-293.

94. Kitazono, M., Rao, V. K., Robey, R., Aikou, T., Bates, S., Fojo, T., and Goldsmith, M. E. Histone deacetylase inhibitor FR901228 enhances adenovirus infection of hematopoietic cells. (2002) Blood 99, 2248-2251.

95. McCaffrey, P. G., Newsome, D. A., Fibach, E., Yoshida, M., and Su, M. S. Induction of gamma-globin by histone deacetylase inhibitors. (1997) Blood 90, 2075-2083.

96. Cao, H., Stamatoyannopoulos, G., and Jung, M. Induction of human gamma globin gene expression by histone deacetylase inhibitors. (2004) Blood 103, 701-709.

97. Skarpidi, E., Vassilopoulos, G., Li, Q., and Stamatoyannopoulos, G. Novel in vitro assay for the detection of pharmacologic inducers of fetal hemoglobin. (2000) Blood 96, 321-326.

98. Li, K. W., Wu, J., Xing, W., and Simon, J. A. Total synthesis of the antitumor depsipeptide FR-901,228. (1996) J. Am. Chem. Soc. 118, 7237-7238.

99. Ahn, J.-M., Boyle, N. A., MacDonald, M. T., and Janda, K. D. Peptidomimetics and peptide backbone modifications. (2002) Mini-Reviews in Medicinal Chemistry 2, 463-473.

100. Hruby, V. J., Ahn, J.-M., and Liao, S. Synthesis of oligopeptide and peptidomimetic libraries. (1997) Curr. Opin. Chem. Biol. 1, 114-119.

101. Mohamadi, F., Richards, N. G. J., Guida, W. C., Liskamp, R., Lipton, M., Caufield, C., Chang, G., Hendrickson, T., and Still, W. C. MacroModel—an integrated software system for modeling organic and bioorganic molecules using molecular mechanics. (1990) J. Comput. Chem. 11, 440-467.

102. Weiner, S. J., Kollam, P. A., and Case, D. A. All-atom force field for simulation of proteins and nucleic acids. (1986) J. Comput. Chem. 7, 230-252.

103. Wang, S.-S. p-Alkoxybenzyl alcohol resin and p-alkoxybenzyloxycarbonylhydrazide resin for solid phase synthesis of protected peptide fragments. (1973) J. Am. Chem. Soc. 95, 1328-1333.

104. Knorr, R., Trzeciak, A., Bannwarth, W., and Gillessen, D. New coupling reagents in peptide chemistry. (1989) Tetrahedron Lett. 30, 1927-1930.

105. Wang, D.-F., Helquist, P., Wiech, N. L., and Wiest, O. Toward selective histone deacetylase inhibitor design: Homology modeling, docking studies, and molecular dynamics simulations of human class I histone deacetylases. (2005) J. Med. Chem. 48, 6936-6947.

106. Brehm, A., Miska, E. A., McCance, D. J., Reid, J. L., Bannister, A. J., and Kouzarides, T. Retinoblastoma protein recruits histone deacetylase to repress transcription. (1998) Nature 391, 597.

107. Lernercier, C., Verdel, A., Galloo, B., Curtet, S., Brocard, M. P., and Khochbin, S. mHDA1/HDAC5 histone deacetylase interacts with and represses MEF2A transcriptional activity. (2000) J. Biol. Chem. 275, 15594.

108. Yoshida, M., Matsuyama, A., Komatsu, Y., and Nishino, N. From discovery to the coming generation of histone deacetylase inhibitors. (2003) Curr. Med. Chem. 10, 2351-2358.

109. Somoza, J. R., Skene, R. J., Katz, B. A., Mol, C., Ho, J. D., Jennings, A. J., Luong, C., Arvai, A., Buggy, J. J., Chi, E., Tang, J., Sang, B.-C., Verner, E., Wynands, R., Leahy, E. M., Dougan, D. R., Snell, G., Navre, M., Knuth, M. W., Swanson, R. V., Mcree, D. E., and Tari, L. W. Structural snapshots of human HDAC8 provide insights into the class I histone deacetylases. (2004) Structure 12, 1325-1334.

110. Vannini, A., Volpari, C., Filocamo, G., Caroli Casavola, E., Brunetti, M., Renzoni, D., Chakravarty, P., Paolini, C., De Francesco, R., Gallinari, P., Steinckuhler, C., and Di Marco, S. Crystal structure of a eukaryotic Zn-dependent histone deacetylase, human HDAC8, complexed with a hydroxamide acid inhibitor. (2004) Proc. Natl. Acad. Sci. U.S.A. 101, 15064-15069.

111. Jensen, K. J., Alsina, J., Songster, M. F., Vagner, J., Albericio, F., and Barany, G. Backbone amide linker (BAL) strategy for solid-phase synthesis of C-terminal-modified and cyclic peptides. (1998) J. Am. Chem. Soc. 120, 5441-5452.

112. Pace, B. S., Shartava, A., Pack-Mabien, A., Mulekar, M., Ardia, A., and Goodman, S. R. Effects of N-acetylcysteine on dense cell formation in sickle cell disease. (2003) Am. J. Hematol. 73, 26-32.

What is claimed is:

1. A pharmaceutical composition comprising:
a therapeutically effective amount of a compound and one or more pharmaceutically acceptable carriers, wherein the compound has the structure

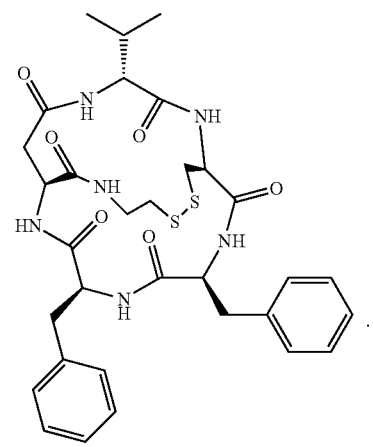

2. The pharmaceutical composition of claim 1, further comprising one or more of diluents, excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof.

3. The pharmaceutical composition of claim 1, wherein the compound comprises the form of a solution, an emulsion, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

4. A compound having the formula:

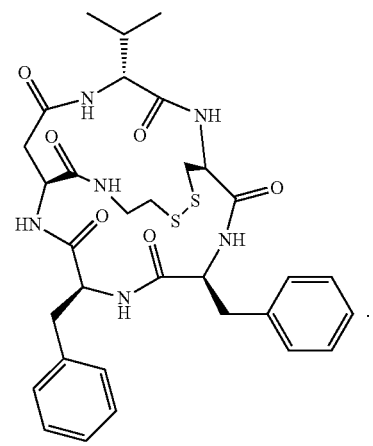

* * * * *